United States Patent
Zheng et al.

(10) Patent No.: US 9,072,774 B2
(45) Date of Patent: Jul. 7, 2015

(54) PORPHYRIN NANOVESICLES

(75) Inventors: Gang Zheng, Toronto (CA); Jonathan F. Lovell, Toronto (CA)

(73) Assignee: UNIVERSITY HEALTH NETWORK, Toronto, Ontario (CA)

( * ) Notice: Subject to any disclaimer, the term of this patent is extended or adjusted under 35 U.S.C. 154(b) by 378 days.

(21) Appl. No.: 13/502,157

(22) PCT Filed: Oct. 5, 2010

(86) PCT No.: PCT/CA2010/001573
§ 371 (c)(1),
(2), (4) Date: Jun. 22, 2012

(87) PCT Pub. No.: WO2011/044671
PCT Pub. Date: Apr. 21, 2011

(65) Prior Publication Data
US 2012/0253191 A1  Oct. 4, 2012

Related U.S. Application Data

(60) Provisional application No. 61/252,367, filed on Oct. 16, 2009.

(51) Int. Cl.
*A61K 9/00* (2006.01)
*A61K 41/00* (2006.01)
*A61K 49/00* (2006.01)
*A61K 47/48* (2006.01)

(52) U.S. Cl.
CPC ....... *A61K 41/0071* (2013.01); *Y10T 428/2991* (2015.01); *A61K 49/0036* (2013.01); *A61K 49/0084* (2013.01); *A61K 47/48053* (2013.01)

(58) Field of Classification Search
CPC .......................... A61K 9/00; A61K 47/88053
USPC ........ 424/9.6, 9.61, 130.1, 400; 540/145, 148
See application file for complete search history.

(56) References Cited

U.S. PATENT DOCUMENTS 5,389,378 A * 2/1995 Madden ......................... 424/450
7,682,603 B2 * 3/2010 Hammer et al. ............. 424/9.61

FOREIGN PATENT DOCUMENTS

| JP | 2006-056807 | 3/2006 |
|---|---|---|
| JP | 2007-277218 | 10/2007 |
| WO | WO 2009/111439 | 9/2009 |
| WO | WO-2009/111439 | * 9/2009 |

OTHER PUBLICATIONS

Komatsu, et al., "Synthesis and Aggregate Morphology of Protoporphyrin IX Derivative Having Phospholipid Residue", Chemistry Letters, 1993, pp. 1949-1952.
Office Action from related Japanese Patent Application No. 2012-533441, dated Jul. 8, 2014, 5 pages.
Babilas et al., "Photodynamic therapy in dermatology—an update", *Photodermatology, Photoimmunology Photomedicine*, 21:142-149, 2005.
Biesaga et al., "Porphyrins in analytical chemistry. A review", *Talanta*, 51:209-224, 2000.
Brown et al., "The present and future role of photodynamic therapy in cancer treatment", *Lancet Oncology*, 5:497-508, 2004.
Chan and Nie, "Quantum Dot Bioconjugates for Ultrasensitive Nonisotopic Detection", *Science*, 281(5385):2016-2018, 1998.
Chen et al., "Liposomal delivery of photosensitizing agents", *Expert Opin. Drug Deliv.*, 2:477-487, 2005.
Dolmans et al., "Photodynamic therapy for cancer", *Perspectives*, 3:380-387, 2003.
Dougherty et al., "Photodynamic Therapy", *J. Natil. Cancer Inst.*, 90:889-905, 1998.
Drain et al., "Self-Organized Phorphyrinic Materials", *Chem. Rev.*, 109:1630-1658, 2009.
Ghoroghchian et al., "Near-infrared-emissive polymersomes: Self-assembled soft matter for in vivo optical imaging", *PNAS*, 102(8):2922-2927, 2005.
Ghosh et al., "Gold nanoparticles in delivery applications", *Advanced Drug Delivery Reviews*, 60:1307-1315, 2008.
Hansen et al., "Attachment of antibodies to sterically stabilized liposomes: evaluation, comparison and optimization of coupling procedures", *Biochimica et Biophysica Acta*, 1239:133-144, 1995.
Haran et al., "Transmembrane ammonium sulfate gradients in liposomes produce efficient and stable entrapment of amphipathic weak bases", *Biochimica et Biophysica Acta*, 1151:201-215, 1993.
Huang et al., "Cancer Cell Imaging and Photothermal Therapy in Near-Infrared Region by Using Gold Nanorods", *J. Am. Chem. Soc.*, 128:2115-2120, 2006.
International Search Report issued in PCT Patent Application No. PCT/CA2010/001573, dated Jan. 14, 2011.
Klostranec and Chan, "Quantum Dots in Biological and Biomedical Research: Recent Progress and Present Challenges", *Advanced Materials*, 18:1953-1964, 2006.
Komatsu et al., Self-Organized Lipid-Porphyrin Bilayer Membranes in Vesicular Form: Nanostructure, Photophysical Properties, and Dioxygen Coordination, *Chem. Eur. J.*, 8(23):5469-5480, 2002.
Lal et al., "Nanoshell-Enabled Photothermal Cancer Therapy: Impending Clinical Impact", *Accounts of Chemical Research*, 41(12):1842-1851, 2008.
Lee and Low, "Delivery of Liposomes into Cultured KB Cells via Folate Receptor-mediated Endocytosis", *The Journal of Biological Chemistry*, 269(5):3196-3204, 1994.
Lewinski et al., "Cytotoxicity of Nanoparticles", *Small Journal*, 4(2):26-49, 2008.
Lovell et al., "FRET Quenching of Photosensitizer Singlet Oxygen Generation", *J. Phys. Chem. B*, 113:3203-3211, 2009.

(Continued)

*Primary Examiner* — Michael G Hartley
*Assistant Examiner* — Jagadishwar Samala
(74) *Attorney, Agent, or Firm* — Norton Rose Fulbright US LLP; Scott D. Rothenberger

(57) ABSTRACT

The application relates to a nanovesicle comprising a bilayer of at least 15 mol % porphyrin-phospholipid conjugate, wherein the conjugate comprises a porphyrin, porphyrin derivative or porphyrin analog covalently attached to the phospholipid side chain. The nanovesicle can be used for photothermal therapy, photoacoustic imaging, and fluorescence imaging. The application also discloses a method of preparing the said nanovesicle.

23 Claims, 21 Drawing Sheets

(56) References Cited

OTHER PUBLICATIONS

Mason et al., "A Method for the Synthesis of Isomerically Pure Saturated Mixed-Chain Phosphatidylcholines", *Analytical Biochemistry*, 113:96-101, 1981.

Matos et al., "Effect of Core Structure on Photophysical and Hydrodynamic Properties of Porphyrin Dendrimers", *Macromolecules*, 33:2967-2973, 2000.

Miller and Lown, "Immunophyotodynamic Therapy: Current Developments and Future Prospects", *Drug Dev. Res.*, 42:182-197, 1997.

Nagayasu et al., "The size of liposomes: a factor which affects their targeting efficiency to tumors and therapeutic activity of liposomal antitumor drugs", *Advanced Drug Delivery Review*, 40:75-87, 1999.

Nel et al., "Toxic Potential of Materials at the Nanolevel", *Science*, 311:622-627, 2006.

O'Neal et al., "Photo-thermal tumor ablation in mice using near infrared-absorbing nanoparticles", *Cancer Letters*, 209:171-176, 2004.

Oraevsky et al., "Laser opto-acoustic tomography for medical diagnostics: principles", *SPIE*, 2676:22-31, 2003.

Oraevsky and Karabutov, "Optoacoustic Tomography", *Biomedical Photonics Handbook*, 34:1-34, 2003.

Papahadjopoulos et al., "Sterically stabilized liposomes: Improvements in pharmacokinetics and antitumor therapeutic efficacy", *Proc. Natl. Acad. Sci.*, 88:11460-11464, 1991.

Peer et al., "Nanocarriers as an emerging platform for cancer therapy", *Nature Nanotechnology*, 2:751-760, 2007.

Riske et al. "Giant Vesicles under Oxidateive Stress Induced by a Membrane-Anchored Photosensitizer", *Biophys. J.*, 97:1362-1370, 2009.

Schnyder et al., "Targeting of skeletal muscle in vitro using biotinylated immunoliposomes", *Biochem. J.* 337:61-67, 2004.

Shi and Pardridge, "Noninvasive gene targeting to the brain", *PNAS*, 97(13):7567-7572, 2000.

Sternberg and Dolphin, "Porphyrin-based Photosensitizers for Use in Photodynamic Therapy", *Tetrahedron*, 54:4151-4202, 1998.

Storhoff et al., "Homogeneous detection of unamplified genomic DNA sequences based on colorimetric scatter of gold nanoparticle probes", *Nature Biotechnology*, 22(7):883-887, 2004.

Sudimack and Lee, "Targeted drug delivery via the folate receptor", *Advanced Drug Delivery Reviews*, 41:147-162, 2000.

Tsuda et al., "Fully Conjugated Porphyrin Tapes with Electronic Absorption Bands That Reach Into Infrared", *Science*, 293:79-82, 2001.

Vakoc et al, "Three-dimensional microscopy of the tumor microenvironment in vivo using optical frequency domain imaging", *Nature Medicine*, 15(10):1219-1224, 2009.

Wang, "Multiscale photoacoustic microscopy and computed tomography", *Nature Photonics*, 3:503-509, 2009.

Wang et al., "Stable porphyrin vesicles formed in non-aqueous media and dried to produce hollow shells", *Chem. Comm.*, pp. 1353-1355, 2009.

Weissleder and Pittet, "Imaging in the era of molecular oncology", *Nature*, 452:580-589, 2008.

Woodburn et al., "CME Photodynamic Therapy for Choroidal Neovasularization", *Retina* (Philadelphia, Pa.), 22(4):391-405, 2002.

Xu and Wang, "Photoacoustic imaging in biomedicine", *Review of Scientific Instruments*, 77(041101):1-22, 2006.

Yguerabide and Yguerabide, "Light-Scattering Submicroscopic Particles as Highly fluorescent Analogs and their Use as Tracer Labels in Clinical and Biological Applications", *Analytical Biochemistry*, 262:157-176, 1998.

Zheng et al., "Low-Density Lipoprotein Reconstituted by Pyropheophorbide Cholesteryl Oleate as Target-Specific Photosensitizer", *Bioconjugate Chem.*, 13:392-396, 2002.

Office Action from related Chinese Application No. 2010800467377, dated Jun. 5, 2014, 14 pages.

* cited by examiner

PORPHYRIN NANOVESICLES

The present application is a national phase application under 35 U.S.C. §371 of International Application No. PCT/CA2010/001573 filed Oct. 5, 2010 which claims priority to U.S. Provisional Application 61/252,367 filed Oct. 16, 2009, the entire text and figures of which disclosures are incorporated herein by reference without disclaimer.

FIELD OF THE INVENTION

This invention relates to the field of nanovesicles and, more specifically, to porphysomes, nanovesicles with porphyrin bilayers formed from porphyrin conjugated to a phospholipid side chain.

BACKGROUND OF THE INVENTION

Therapeutic and diagnostic techniques benefitting from components that heavily absorb light include fluorescent and colorimetric detection[1,2], photothermal and photodynamic therapy[3-5], photoacoustic tomography (also known as optoacoustic tomography)[6-9], optical frequency domain imaging[10], and multimodal techniques[11], amongst others. Since inorganic nanoparticles interact strongly with light, they can be used as agents for these techniques. For instance, quantum dots are valuable fluorescent probes and have extinction coefficients in the range of $10^5$ to $10^6$ $M^{-1}$ $cm^{-1}$,[12]. Gold nanoparticles are useful for colorimetric detection, photothermal and photoacoustic techniques owing to their much higher extinction coefficients, on the order of $10^9$ to $10^{11} M^{-1}$ $cm^{-1}$,[13]. Despite recent progress[14], optically active inorganic nanoparticles have not yet achieved broad clinical implementation, possibly stemming from drug loading that is generally limited to the nanoparticle surface and concerns regarding long-term safety[15-18]. In contrast, organic nanoparticles (including liposomes, micelles, nanospheres and polymersomes) have found extensive human therapeutic applications as a result of robust safety profiles, bioavailability and drug delivery capacity[18]. However, as organic nanoparticles generally do not absorb light in the near infrared, they have been of limited use for biophotonics.

While supramolecular assemblies can be formed by porphyrins, intensely light-absorbing organic small molecules, these constructs have not been thoroughly explored as biological tools owing to a lack of stability, solubility or biophotonic utility[19].

Photodynamic therapy combines a photosensitizer with light to eradicate unwanted cells. Compared to other disease treatments, PDT offers the advantage that only where the light and photosensitizer intersect will cells be killed, so that other tissues and organs in the body are spared from damage. In the past decades, PDT has become established as a viable treatment option for a wide range of ophthalmic[22], dermatologic[23] and in particular oncogenic[24] diseases. PDT has emerged as a useful cancer treatment that can destroy unwanted cells through necrosis or apoptosis induced by cellular damage caused by singlet oxygen[25]. Porphyrin derivatives are the most widely used photosensitizers due to their high singlet oxygen quantum yield and their large extinction coefficients[26]. However, since conventional porphyrins are hydrophobic molecules, often they must be chemically modified to become more hydrophilic or a delivery vehicle must be used. As such, photosensitizer delivery is an important element of PDT. Liposomal formulations of photosensitizers have found widespread implementation[27] and also have shown commercial success (Novartis' Visudyne; Biotec's Foscan, Foslip and Fospeg).

Although PDT has fewer side effects compared to many other treatments, damage to tissue surrounding the target is a limiting factor for more effective treatment. Therefore, PDT that is targeted towards certain unwanted cells is an attractive concept. However, attempts to use antibodies to redirect photosensitizers have been hampered due to the low number of photosensitizers that can be conjugated to an antibody before interfering with antibody function[28]. Directing photosensitizer-loaded liposomes to targets via antibodies is not practical since photosensitizers redistribute rapidly from liposomes to serum proteins in vivo. Photothermal therapy is a promising disease treatment method in which light is transduced into heat at target sites. The heat produced then destroys the local tissues. Photoacoustic imaging is an emerging imaging technique that relies on nanosecond pulsed lasers and photothermal expansion to generate sound waves that can provide the deepest depth structural resolution of any optical technique.

SUMMARY OF THE INVENTION

According to one aspect, there is provided a nanovesicle comprising a bilayer of at least 15 molar % porphyrin-phospholipid conjugate, wherein the porphyrin-phospholipid conjugate comprises one porphyrin, porphyrin derivative or porphyrin analog covalently attached to a lipid side chain, preferably at the sn-1 and the sn-2 position, of one phospholipid.

According to a further aspect, there is provided a method of preparing a nanovesicle, comprising:
   a. mixing a porphyrin-phospholipid conjugate in buffer, wherein the porphyrin-phospholipid conjugate comprises one porphyrin, porphyrin derivative or porphyrin analog covalently attached to a lipid side chain, preferably at the sn-1 and/or the sn-2 position, of one phospholipid;
   b. extruding the mixture of step (a) to yield a porphyrin-phospholipid bilayer nanovesicle comprising a bilayer of at least 15 molar % porphyrin-phospholipid conjugate.

According to a further aspect, there is provided a method of preparing a nanovesicle, comprising:
   a. mixing a porphyrin-phospholipid conjugate in buffer, wherein the porphyrin-phospholipid conjugate comprises one porphyrin, porphyrin derivative or porphyrin analog covalently attached to a lipid side chain, preferably at the sn-1 and/or the sn-2 position, of one phospholipid; and
   b. sonicating the mixture of step (a) to yield a porphyrin-phospholipid bilayer nanovesicle comprising a bilayer of at least 15 molar % porphyrin-phospholipid conjugate.

According to a further aspect, there is provided a method of performing photodynamic therapy on a target area in a subject comprising:
   a. providing the nanovesicle described herein;
   b. administering the nanovesicle to the subject; and
   c. irradiating the nanovesicle at the target area with a wavelength of light, wherein the wavelength of light activates the porphyrin-phospholipid conjugate to generate singlet oxygen.

According to a further aspect, there is provided a method of performing photothermal therapy on a target in a subject comprising:
   a. providing the nanovesicle described herein;
   b. administering the nanovesicle to the subject; and
   c. irradiating the nanovesicle at the target area with a wavelength of light, wherein the wavelength of light increases the temperature of nanovesicle.

According to a further aspect, there is provided a method of imaging a target area in a subject, comprising
  a. providing the nanovesicle of described herein;
  b. administering the nanovesicle to the subject;
  c. irradiating the nanovesicle at the target area with a wavelength of light, wherein the nanovesicle emits a photoacoustic signal in response to the wavelength of light; and
  d. measuring and/or detecting the photoacoustic signal at the target area.

According to a further aspect, there is provided a method of imaging a target area in a subject, comprising
  a. providing the nanovesicle described herein;
  b. administering the nanovesicle to the subject; and
  c. measuring and/or detecting the fluorescence at the target area.

According to a further aspect, there is provided a use of the nanovesicle of described herein for performing photodynamic therapy.

According to a further aspect, there is provided a use of the nanovesicle described herein for performing photothermal therapy.

According to a further aspect, there is provided a use of the nanovesicle described herein for performing photoacoustic imaging.

According to a further aspect, there is provided a use of the nanovesicle described herein for performing fluorescence imaging.

According to a further aspect, there is provided a use of the nanovesicle described herein for performing photothermal therapy in combination with the delivery of a chemotherapeutic drug such as doxorubicin loaded within the nanovesicles.

BRIEF DESCRIPTION OF THE DRAWINGS

Embodiments of the invention may best be understood by referring to the following description and accompanying drawings. In the drawings.

DETAILED DESCRIPTION OF THE PREFERRED EMBODIMENTS

Figure 1:
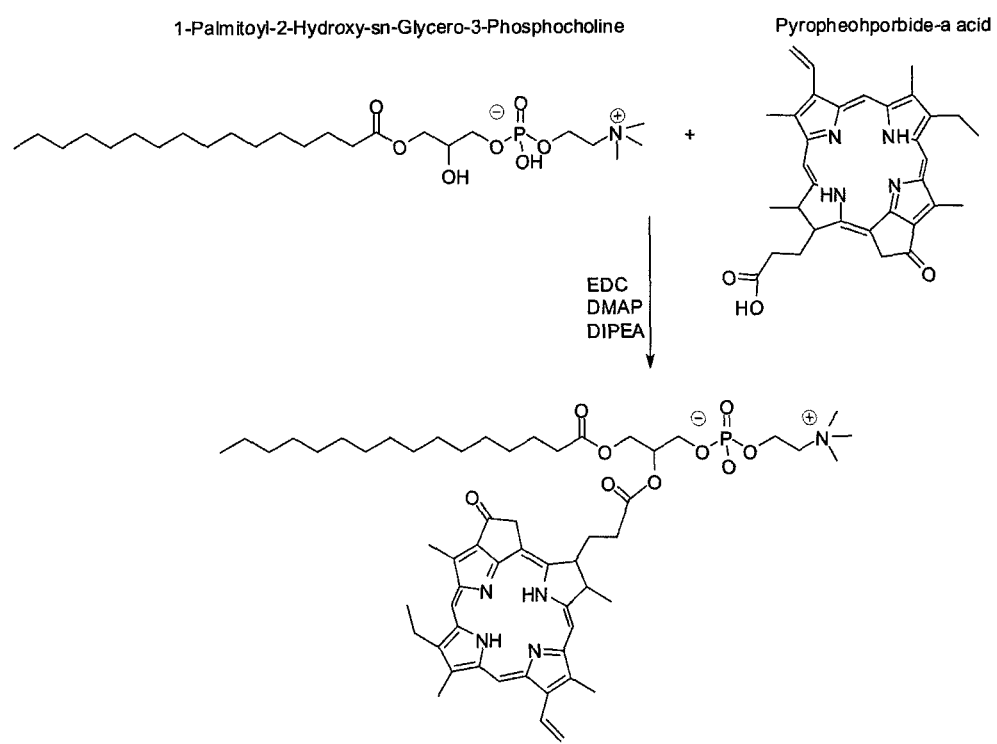
FIG. 1 shows synthesis of the pyropheophorbide-lipid conjugate (denoted Pyro-lipid).

There is herein described "porphysomes"; organic nanoparticles self-assembled from subunits of phospholipid-porphyrin conjugates that exhibit liposome-like structure and loading capacity, structure-dependent nanoscale phototransductive properties, excellent biocompatibility, and have promise for a diversity of biophotonic applications. Other porphyrin vesicles and diblock copolymers have been described that incorporate porphyrin subunits, but low porphyrin density resulted in lesser extinction coefficients and an absence of the characteristic significant fluorescence self-quenching that generates the novel properties of porphysomes[20,21].

Porphyrins are often used in nanostructure applications, including the formation of dendrimers[29] and nanowires[30]. Recently, water insoluble spherical assemblies of porphyrins were described[31]. However, compared to porphysomes, these nanoparticles were developed with a different type of subunit that was shown to be conducive to fluorescence-self quenching and phototransduction.

In some embodiments, the porphysome comprises a porphyrin-lipid conjugated bilayer comprising approximately 100,000 porphyrin molecules per porphysome. Since they are formed and stabilized by the porphyrin subunits, porphysomes can be targeted to cells using a range of cellular targeting moieties. Porphysomes are highly versatile, with the capacity to be formed with different types of porphyrins, with the capacity to chelate different types of metals, and with the capacity to be formed with varying sizes as described in further detail below. Further, porphysomes demonstrate novel nanoscale properties, with high quenching and photothermal transduction efficiency prior to activation.

While insertion of porphyrins into liposomes for photodynamic therapy (PDT) has attracted attention, porphysomes offer 2 significant advantages: 1) a payload 1-2 orders of magnitude higher than any other liposomal PDT formulation and 2) for the first time, a method to permit the targeting a large number of photosensitizers to a specific location in the body (other formulations redistribute to plasma proteins upon administration). Insertion of various metals into the porphyrin lipid did not interfere with porphysome formation and stable zinc and palladium bilayered porphysomes were generated, opening up new avenues for targeted metal therapies. Porphysomes could be formed from different types of porphyrin and could be tailored to various sizes. Porphysomes displayed unprecedented fluorescence and singlet oxygen activation, orders of magnitude greater than anything previously described. Prior to activation, in their highly quenched state, porphysomes dissipated excitation light with a photothermal conversion efficiency comparable to gold nanorods, suggesting porphysomes can be useful as photothermal and photoacoustic probes. Uptake and activation of folate conjugated porphysomes could be induced by receptor mediated endocytosis in cells expressing the folate receptor and those cells were destroyed upon subsequent light irradiation. As new, targetable and therapeutically active nanoparticles, porphysomes are anticipated to find numerous applications in photodynamic therapy and other areas of research.

The nanovesicles described herein are small, typically less than 200 nm, vesicles (i.e. bubbles or sacs) formed by a membrane comprising a bilayer of phospholipid or derivatives thereof. However, using standard lipid techniques, a person skilled in the art would also be able to generate much larger bilayers such a giant unilamellar vesicles or planar lipid bilayers.

According to one aspect, there is provided a nanovesicle comprising a bilayer of at least 15 molar % porphyrin-phospholipid conjugate, wherein the porphyrin-phospholipid conjugate comprises one porphyrin, porphyrin derivative or porphyrin analog covalently attached to a lipid side chain, preferably at the sn-1 or the sn-2 position, of one phospholipid.

In preferred embodiments, in increasing preference, the nanovesicle comprises at least 25, 34, 45, 55, 65, 75, 85 and 95 molar % porphyrin-phospholipid conjugate.

The porphyrin-phospholipid conjugate making up the nanovesicles of the present invention comprises porphyrins, porphyrin derivatives and porphyrin analogs. Exemplary porphyrins include hematoporphyrin, protoporphyrin and tetraphenylporphyrin. Exemplary porphyrin derivatives include pyropheophorbides, bacteriochlorophylls, chlorophyll a, benzoporphyrin derivatives, tetrahydroxyphenyl chlorins, purpurins, benzochlorins, naphthochlorins, verdins, rhodins, keto chlorins, azachlorins, bacteriochlorins, tolyporphyrins and benzobacteriochlorins. Porphyrin analogs include expanded porphyrin family members (such as texaphyrins, sapphyrins and hexaphyrins), and porphyrin isomers (such as porphycenes, inverted porphyrins, phthalocyanines, and naphthalocyanines).

Preferably, the expanded porphyrin is a texaphyrin, a sapphyrin or a hexaphyrin and the porphyrin isomer is a porphycene, an inverted porphyrin, a phthalocyanine, or a naphthalocyanine.

As used herein, "phospholipid" is a lipid having a hydrophilic head group having a phosphate group and hydrophobic lipid tail.

In some embodiments, the phospholipid in the porphyrin-phospholipid conjugate comprises phosphatidylcholine, phosphatidylethanoloamine, phosphatidylserine or phosphatidylinositol.

Preferably, the phospholipid comprises an acyl side chain of 12 to 22 carbons.

In some embodiments, the porphyrin in the porphyrin-phospholipid conjugate is Pyropheophorbide-a acid. In another embodiment the porphyrin in the porphyrin-phospholipid conjugate is Bacteriochlorophyll derivate.

In some embodiments, the phospholipid in the porphyrin-phospholipid conjugate is 1-Palmitoyl-2-Hydroxy-sn-Glycero-3-Phosphocholine.

In some embodiments, the porphyrin-phospholipid conjugate is Pyro-lipid.

In other embodiments, the porphyrin-phospholipid conjugate is oxy-bacteriochlorophyll-lipid.

In some embodiments, the porphyrin is conjugated to the glycerol group on the phospholipid by a carbon chain linker of 0 to 20 carbons.

In some embodiments, the nanovesicle further comprises PEG, preferably PEG-lipid and further preferably PEG-DSPE. Preferably the PEG or PEG-Lipid is present in an amount of about 5 molar %.

In some embodiments, the nanovesicle is substantially spherical and between about 30 nm at about 200 nm in diameter, preferably about 100 nm in diameter or about 30 nm in diameter.

In some embodiments, the porphyrin-phospholipid conjugate comprises a metal chelated therein, optionally a radioisotope of a metal, preferably Zn, Cu or Pd.

A wide variety of bioactive or therapeutic agents, pharmaceutical substances, or drugs can be encapsulated within the interior of the porphysome.

In some embodiments, the nanovesicle further comprises an active agent encapsulated therein, preferably a therapeutic agent or a diagnostic agent, preferably a chemotherapy agent such as doxorubicin.

The term "therapeutic agent" is art-recognized and refers to any chemical moiety that is a biologically, physiologically, or pharmacologically active substance. Examples of therapeutic agents, also referred to as "drugs", are described in well-known literature references such as the Merck Index, Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject.

A "diagnostic" or "diagnostic agent" is any chemical moiety that may be used for diagnosis. For example, diagnostic agents include imaging agents, such as those containing radioisotopes such as indium or technetium; contrasting agents containing iodine or gadolinium; enzymes such as horse radish peroxidase, GFP, alkaline phosphatase, or β-galactosidase; fluorescent substances such as europium derivatives; luminescent substances such as N-methylacrydium derivatives or the like.

In some embodiments, the nanovesicle further comprises targeting molecule, preferably an antibody, peptide, aptamer or folic acid.

"Targeting molecule" is any molecule that can direct the nanovesicle to a particular target, for example, by binding to a receptor or other molecule on the surface of a targeted cell. Targeting molecules may be proteins, peptides, nucleic acid molecules, saccharides or polysaccharides, receptor ligands or other small molecules. The degree of specificity can be modulated through the selection of the targeting molecule. For example, antibodies typically exhibit high specificity. These can be polyclonal, monoclonal, fragments, recombinant, or single chain, many of which are commercially available or readily obtained using standard techniques.

In some embodiments, the bilayer of the nanovesicle further comprises cholesterol, preferably between 30-50 molar % cholesterol.

According to a further aspect, there is provided a method of preparing a nanovesicle, comprising mixing a porphyrin-phospholipid conjugate in buffer, wherein the porphyrin-phospholipid conjugate comprises one porphyrin, porphyrin derivative or porphyrin analog covalently attached to a lipid side chain, preferably at the sn-1 and/or the sn-2 position, of one phospholipid; and extruding the mixture to yield a porphyrin-phospholipid bilayer nanovesicle comprising a bilayer of at least 15 molar % porphyrin-phospholipid conjugate.

Preferably, the porphyrin-phospholipid conjugate comprises a metal chelated therein.

According to a further aspect, there is provided a method of preparing a nanovesicle, comprising mixing a porphyrin-phospholipid conjugate in buffer, wherein the porphyrin-phospholipid conjugate comprises one porphyrin, porphyrin derivative or porphyrin analog covalently attached to a lipid side chain, preferably at the sn-1 and/or the sn-2 position, of one phospholipid; and sonicating the mixture to yield a porphyrin-phospholipid bilayer nanovesicle comprising a bilayer of at least 15 molar % porphyrin-phospholipid conjugate.

According to a further aspect, there is provided a method of performing photodynamic therapy on a target area in a subject comprising providing the nanovesicle described herein; administering the nanovesicle to the subject; and irradiating the nanovesicle at the target area with a wavelength of light, wherein the wavelength of light activates the porphyrin-phospholipid conjugate to generate singlet oxygen. Preferably, the nanovesicle is irradiated in an unquenched state.

According to a further aspect, there is provided a method of performing photothermal therapy on a target in a subject comprising providing the nanovesicle described herein;

administering the nanovesicle to the subject; and irradiating the nanovesicle at the target area with a wavelength of light, wherein the wavelength of light increases the temperature of nanovesicle. Preferably, the nanovesicle is irradiated in a quenched state.

According to a further aspect, there is provided a method of imaging a target area in a subject, comprising providing the nanovesicle of described herein; administering the nanovesicle to the subject; irradiating the nanovesicle at the target area with a wavelength of light, wherein the nanovesicle emits a photoacoustic signal in response to the wavelength of light; and measuring and/or detecting the photoacoustic signal at the target area.

According to a further aspect, there is provided a method of imaging a target area in a subject, comprising providing the nanovesicle described herein; administering the nanovesicle to the subject; and measuring and/or detecting the fluorescence at the target area.

According to a further aspect, there is provided a use of the nanovesicle of described herein for performing photodynamic therapy.

According to a further aspect, there is provided a use of the nanovesicle described herein for performing photothermal therapy.

According to a further aspect, there is provided a use of the nanovesicle described herein for performing photoacoustic imaging.

According to a further aspect, there is provided a use of the nanovesicle described herein for performing fluorescence imaging.

The following examples are illustrative of various aspects of the invention, and do not limit the broad aspects of the invention as disclosed herein.

EXAMPLES

Materials and Methods

Synthesis of Pyro-Lipid (Lyso-Phosphatidyl Choline (16:0)-Pyropheophorbide)

The following were combined in 10 mL anhydrous dichloromethane: 49.6 mg (0.1 mmol) 1-palmitoyl-2-hydroxy-sn-glycero-3-phosphocholine (Avanti Polar Lipids), 26.7 mg (0.05 mmol) pyropheophorbide-a acid (Purified from Spirulina Pacifica, as described previously), 0.05 mmol EDC (Sigma), 0.025 mmol DMAP (Sigma) and 1 drop of DIPEA (Sigma). The reaction mixture was stirred at room temperature under argon in the dark for 48 hours. The solvent was evaporated and the residue was subjected to thin layer chromatography (TLC) purification (20×20 cm pre-coated silica gel TLC plate with fluorescence indicator, 1.5 mm in thickness). Chloroform-methanol-glacial acetic acid-water 65:25:8:2 (V:V) was used as the solvent. The major band with Rf=0.4 was isolated from the plate and eluted giving a final yield of 45%. The Pyro-lipid purity and identity was confirmed with HPLC and mass spectrometry and was then dried under nitrogen and stored under argon at −20° C. in 1 umol aliquots.

Synthesis of OxyBacteriochlorophyl-Lipid

At room temperature, 49.6 mg (0.1 mmol) 1-palmitoyl-2-hydroxy-sn-glycero-3-phosphocholine, 30.5 mg (0.05 mmol) bacteriopheophorbide-a acid, 0.05 mmol EDC, 0.025 mmol DMAP and 1 drop of DIPEA were added to 10 mL anhydrous DCM. The reaction mixture was stirred at room temperature under argon in dark for 48 hrs. TLC showed there was still Bchl acid spot by comparing with pure Bchl acid. The solvent was evaporated and the residue was subjected to TLC plate purification (20×20 cm pre-coated silica gel TLC plate with fluorescence indicator, 1.5 mm in thickness). Chloroform-methanol-glacial acetic acid-water 65:25:8:2 (V:V) was used as developing system. The final product was obtained in 38% yield with $R^f$=0.4. The final product spontaneously oxidized to yield oxy Bchl-lipid, which was verified by mass spectrometery. After purification, the purity and mass spectra were confirmed by analytical HPLC-MS. The lipid was aliquoted, dried and stored under argon at −20° C.

Generation of Metallic Pyro-Lipid

To generate porphyrin-lipid conjugates with a chelated metal, 10 fold excess free zinc acetate or palladium chloride was incubated with Pyro-lipid in methanol for 1 hour at room temperature under argon. Free metal was removed by 5 butanol water extractions. The metal porphyrin lipid was then aliquoted, dried and stored under argon at −20° C. The stable metal incorporation, purity and identity of the porphyrin lipids was confirmed by HPLC and mass spectrometry Formation of Standard Porphysomes In the standard preparation, 95 molar % porphyrin-lipid was dissolved in methanol with 5 molar % distearoyl-sn-glycero-3-phosphoethanolamine-N-[methoxy(polyethylene glycol)-2000 (PEG-PE) dissolved in chloroform or 4% PEG-PE supplemented with 1% 1,2-distearoyl-sn-glycero-3-phosphoethanolamine-N-[folate(polyethylene glycol)-2000 (Folate-PEG-PE) in chloroform and were dried under a stream of nitrogen gas and further dried under vacuum for 1 h. The lipid film was stored at −20° C. under argon gas until hydration with phosphate buffered saline (PBS, 150 mM NaCl, 10 mM phosphate, pH 7.4) and then subjected to five freeze-thaw cycles. The porphysome suspension was extruded 15 times using an Avanti Mini-Extruder through a 100 nm pore size polycarbonate membrane at 65° C. Porphysomes were stored at 4° C. under argon until use. The usual porphysome concentration was 0.5 mg/mL.

Formation of Small 30 nm Porphysomes

To form small 30 nm porphysomes, a pure porphyrin-lipid film was generated with 0.1 mg porphyrin-lipid and dried under nitrogen and vacuum. The film was rehydrated with 200 uL of water and was sonicated for 10 minutes at 55° C. The small porphysomes were stored at 4° C. under argon until use Characterization of Size and Shape of Porphysomes Liposome size was measured using a Malvern Nanosizer (Malvern Instruments Ltd., Worcestershire, UK). Liposome solutions were diluted in PBS and three measurements were performed with 15 runs each and the results averaged.

Characterization of Activation Potential of Porphysomes

Emission spectra were recorded by a Fluoromax fluorometer (Horiba JobinYvon, Edison, N.J.) using 2 nm slit widths. Liposomes containing Pyro and Pyro-Lipid were excited at 420 nm and those containing NBD were excited at 470 nm. Fluorescence intensity was collected from 600 nm to 750 nm and 500 nm to 600 nm for Pyro/Pyro-Lipid and NBD respectively. The fluorescence fold self-quenching $F/F_0$ of each sample was determined by dividing its fluorescence in the presence of 0.5% Triton X-100 by its fluorescence in the absence of the detergent.

Characterization of Photothermal Properties of Porphysomes

Five uL drops of the indicated solutions were placed on a piece of parafilm and irradiated with a 670 nm laser with 150 mW output. Temperature was monitored using a temperature calibrated infrared camera (Mikroshot).

Characterization of Photoacoustic Properties of Porphysomes

Photoacoustic measurements were carried out using a Ti:Saphire tunable laser setup with an ultrasound transducer as previously described.[22] Measurements were carried out at 760 nm using oxybacteriochlorophyll porphysomes in PBS solution. The photoacoustic signal of porphysomes was compared to whole bovine blood and also compared to porphysomes that had been lysed with 1% Triton X-100. For in vivo studies, sentinel lymph node and lymphatic vessels mapping with porphysomes was performed using Sprague-Dawley rats (200 g) and a 100 µL of 9 nM porphysomes in injection on left forepaw. The region of interest was shaved prior to injection and photoacoustic measurements.

Differential Scanning Calorimetry

Differential scanning calorimetry was performed on 5 mg/ml samples of DMPC, HSPC, Lyso PC and Pyro-Lipid in PBS using a calorimetry Sciences Corp. 6100 Nano Differential Scanning calorimeter (Lindon, Utah). Samples were placed in a vacuum for 30 min prior to measurement. A scan rate of 1° C./min was used for all samples. PBS was used as the reference and one scan cycle of PBS was used as the baseline. For each lipid, three cooling and heating scans were performed and the results averaged to determine the phase transition temperature of the lipids.

Confocal Microscopy Studies

KB cells were continually cultured in folate free RPMI 1640 media (Invitrogen) with 10% FBS. Cells were seeded in an 8 chamber confocal chamber with 40,000 cells per well the day prior to imaging. Media was removed and the cells were incubated with porphysomes in the folate free media without serum. Cells were imaged with a confocal microscope (Olympus) after a 2 hour porphysome incubation. A 633 nm laser was used for fluorescence excitation.

Cell Viability after Porphysome and PDT Treatment

KB cells were seeded in a 96 well plate in folate free RPMI 1640 media (Invitrogen) with 10% FBS. After 16 h incubation at 37° C. in a 5% $CO_2$ incubator, the media was replaced with RMPI 1640 media containing porphysomes. The cells were incubated for 4 hours and then treated with PDT with 3 different light fluences (1, 5, or 10 $Jcm^{-2}$) using a 670 nm laser with a 120 $mWcm^{-2}$ fluence rate with 0, 24, and 60 s treatment times. Twenty-four hours later, cell viability was assessed using the MTT tracer, 3-(4,5-dimethylthiazol-2-yl)-2,5-diphenyltetrazolium bromide (Invitrogen).

Results and Discussion

Generation of Various Porphysome Subunits

Figure 2:
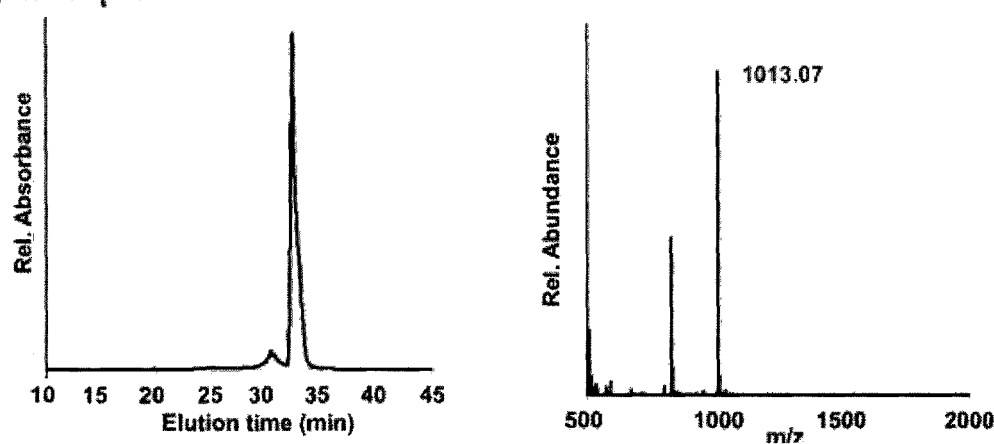
FIG. 2 shows purity and identity of Pyro-Lipid. Left: RP-HPLC chromatogram of Porphyrin-Lipid, indicating good purity. Right: Expected mass spectra of Pyro-lipid.
Figure 3:
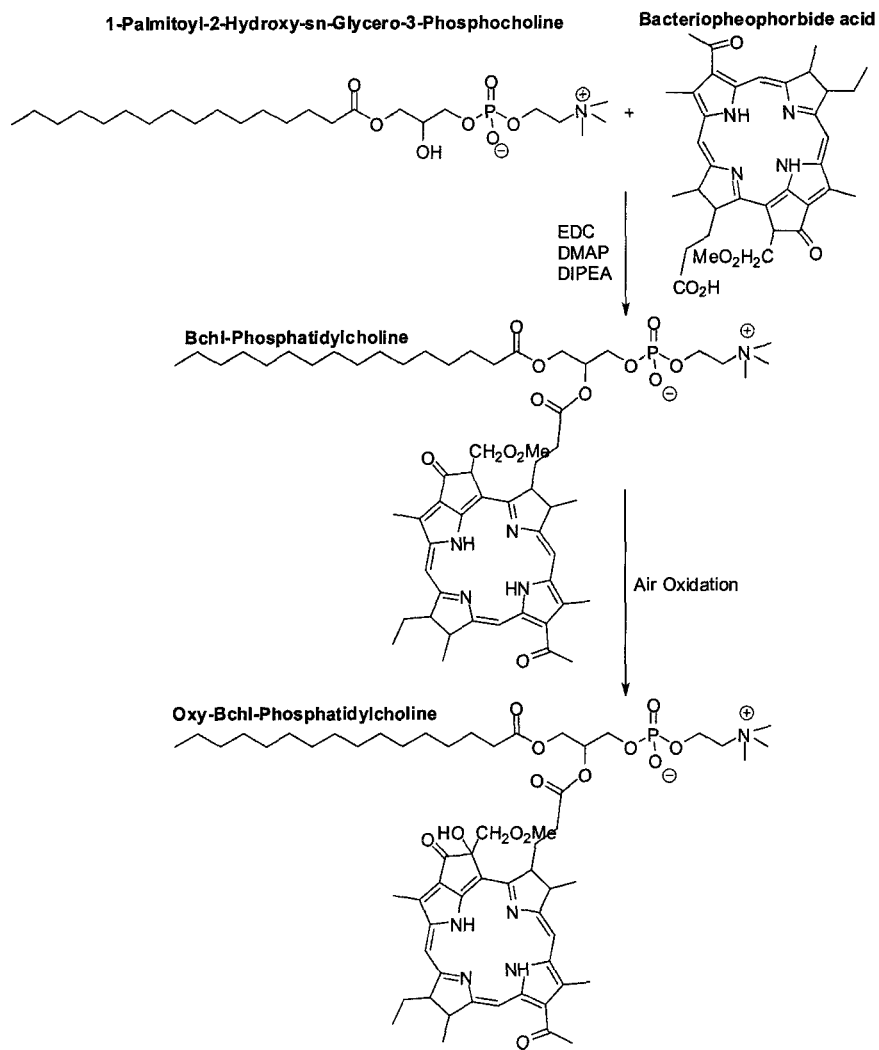
FIG. 3 shows synthesis of Oxy-Bacteriochlorophyll-lipid.
Figure 4:
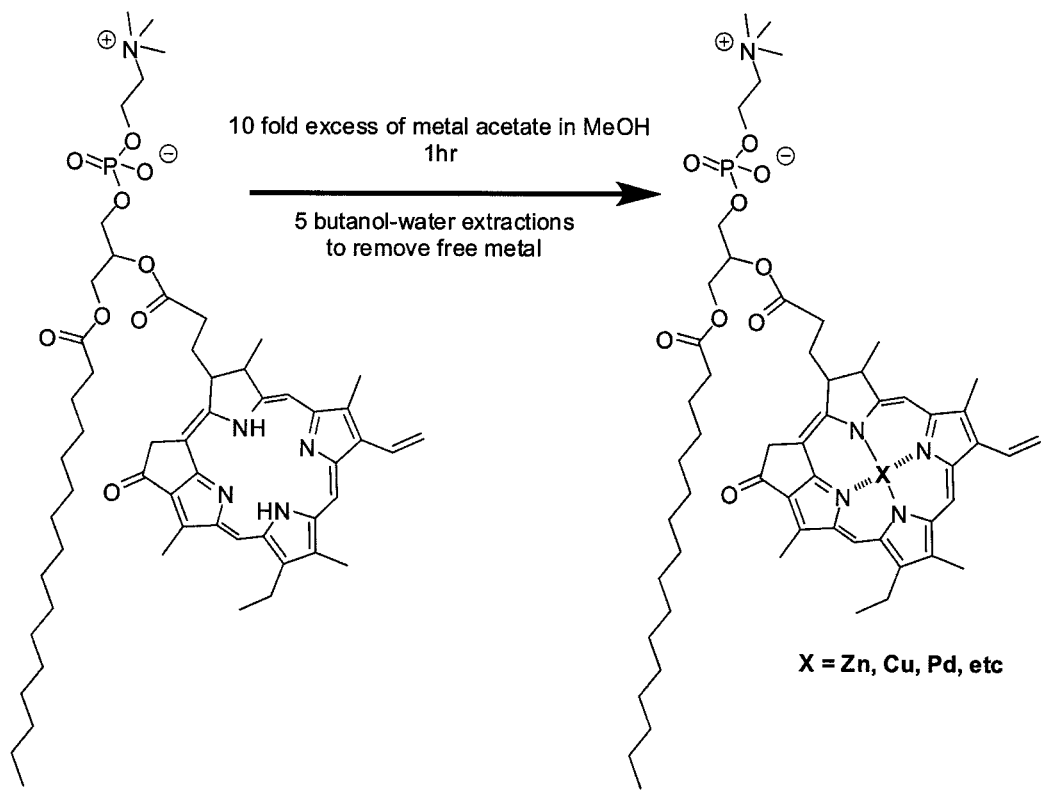
FIG. 4 shows generation of metallic Pyro-lipid.
Figure 5:
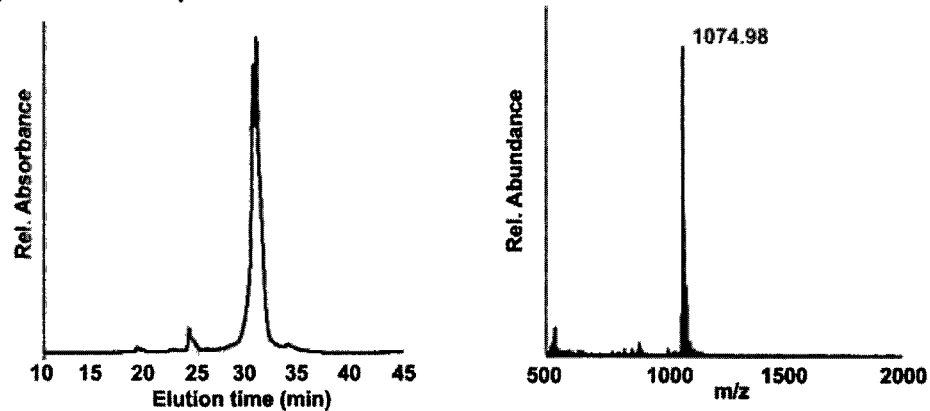
FIG. 5 shows purity and mass of zinc and palladium porphyrin-lipid conjugates. Left panel shows HPLC elution and right panel shows expected mass spectra.
Figure 5:
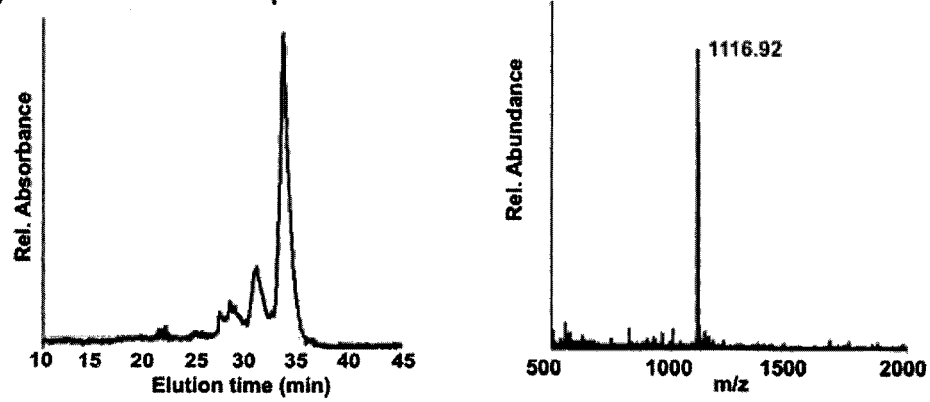

Several different porphyrin-lipid conjugates were developed and used for porphysome formation. Porphysomes were initially formed from subunits of phosphatidyl choline (16:0)-pyropheophorbide (referred to as Pyro-lipid). As shown in FIG. 1, a simple and previously described[32] acylation reaction was used to form Pyro-lipid using commercially available lyso phospholipid and pyropheophorbide, a photosensitizer synthesized in our lab as previously reported[33]. The identity and purity of the compound was confirmed with HPLC and mass spectrometry (FIG. 2). Besides pyropheophorbide, another porphyrin-lipid construct was synthesized using the longer wavelength absorbing bacteriochlorophyll to generate the oxybacteriochlorophyll-lipid (FIG. 3). A wide variety of metal ions are well known be chelated within the porphyrin ring[34]. To examine whether porphysomes could form with a metal chelated bilayer, we generated various metallic Pyro-lipids simply by incubating the Pyro-lipid with an excess of metal ions and removing the free metal ions with several butanol-water extractions, as shown in FIG. 4. The purity and identity of the metallic porphyrin-lipids was confirmed with HPLC and mass spectrometry (FIG. 5).

Generation and Characterization of Porphysomes

Figure 6:
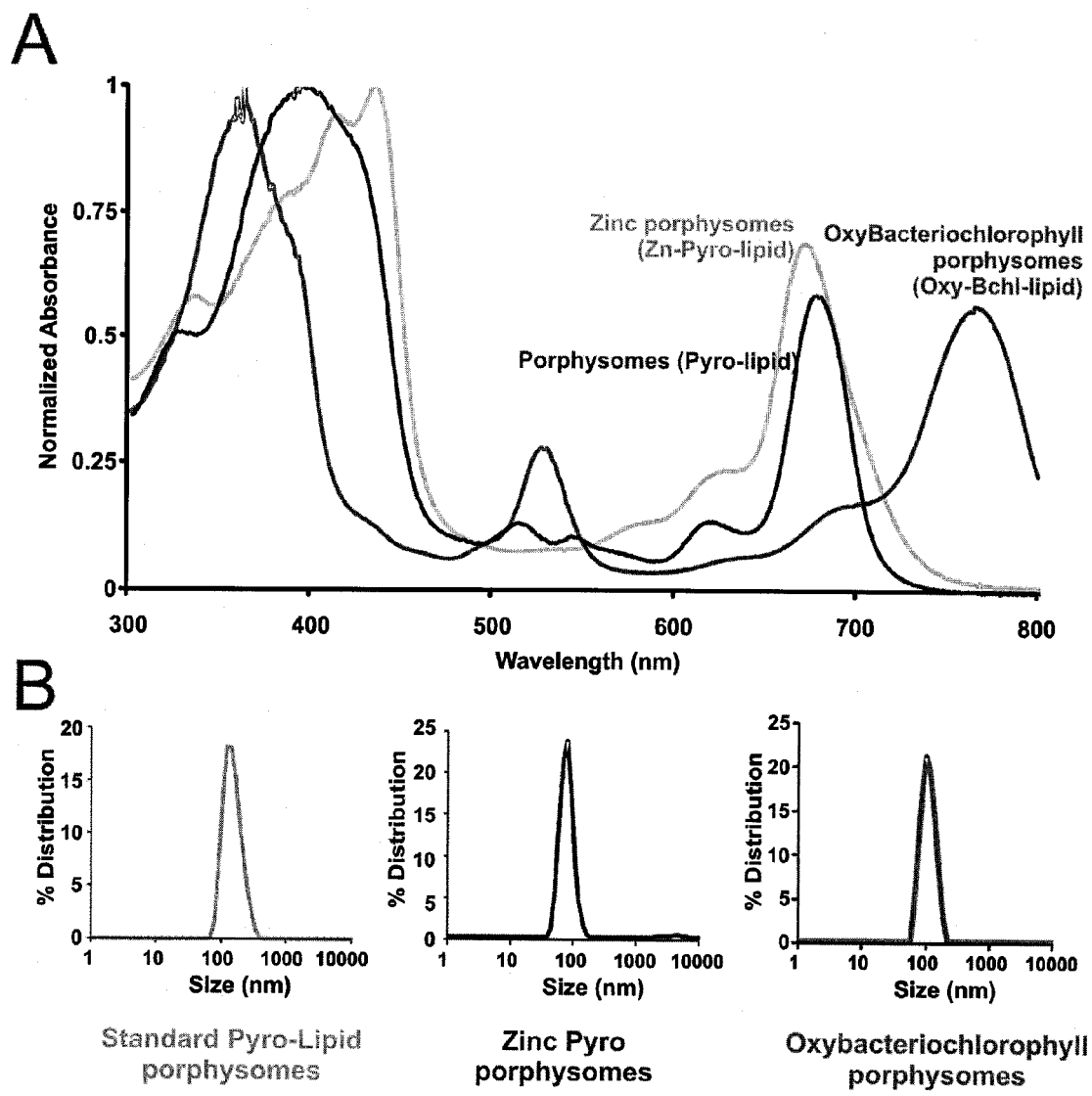
FIG. 6 shows generation of diverse porphysomes. Porphysomes were formed with 95% of various porphyrin-lipids, and 5% polyethylene glycol-2000 conjugated lipid (PEG-lipid) by extrusion with a 100 nm polycarbonate membrane at a concentration of 0.5 mg/mL in PBS. A) Normalized absorption spectra of various porphysomes. B) Dynamic light scattering of various porphysomes showing monodisperse sizes of approximately 100 nm.
Figure 7:
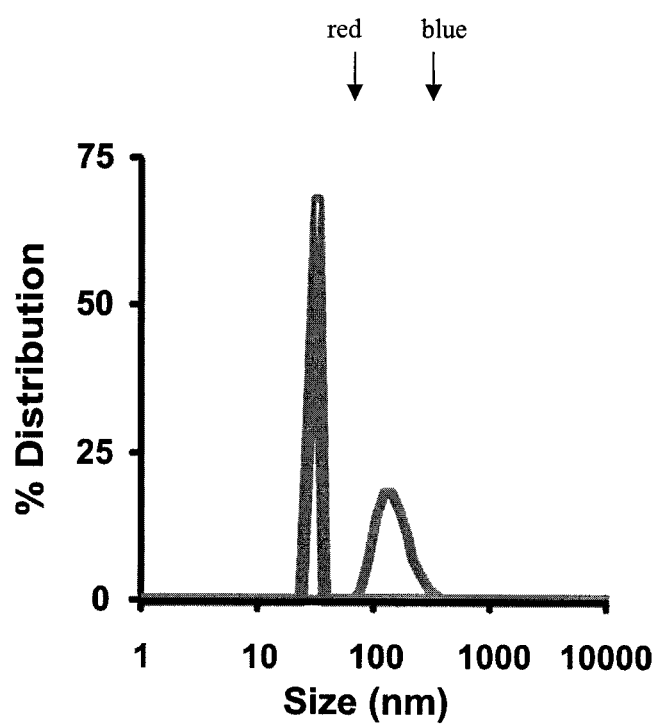
FIG. 7 shows generation of 30 nm porphysomes by sonication. DLS measurements show that Pyro-lipid that was rehydrated and sonicated (red) generated smaller porphysomes than the porphysomes that were created though extrusion through a 100 nm polycarbonate membrane (blue).
Figure 8:
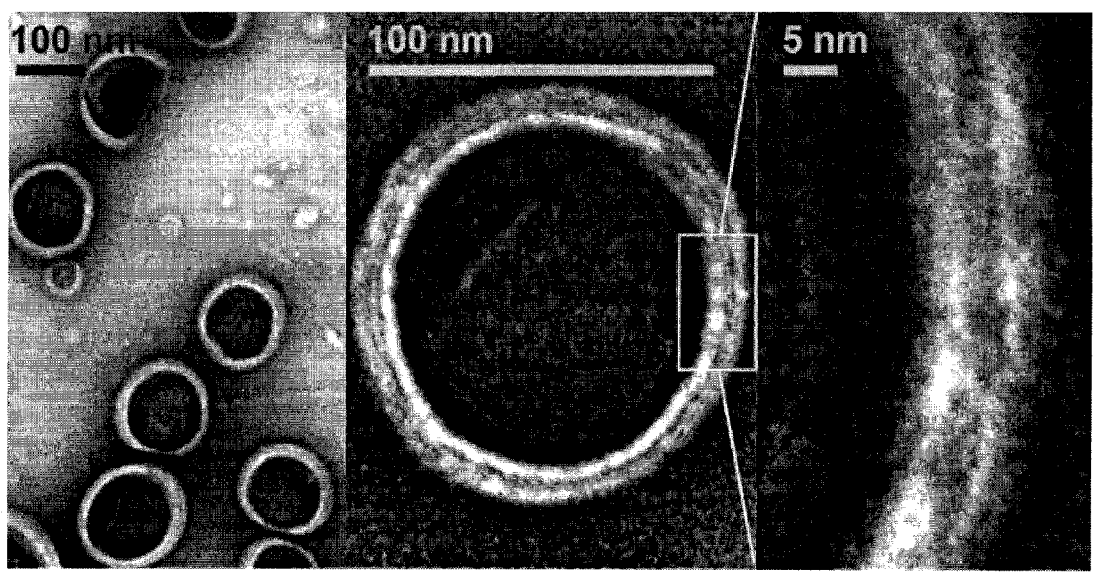
FIG. 8 shows structure of porphysomes revealed by TEM. 1% uranyl acetate stained transmission electron micrograph of porphysomes. Note the features of the bilayer become apparent at higher magnifications.

Porphysomes were generated with phosphate buffered saline (PBS) hydrated porphyrin-lipid films without any difficulties, using with a conventional liposomal extruding apparatus with 100 nm polycarbonate membranes. For biocompatibility, 5 molar % PEG-lipid was included with the 95 molar % porphyrin-lipid. PEG is known to stabilize liposomes and keep them in circulation longer for a better pharmacokinetic profile[35]. Porphysomes were successfully extruded using the various types of porphyrin-lipids generated. The porphysomes had absorption spectra that varied according to the type of porphyrin-lipid used, as shown in FIG. 6A. It is notable that porphysomes possessed strong absorption in the near infrared range, with standard Pyro-lipid porphysomes absorbing 680 nm, and oxybacteriochlorophyll porphysomes absorbing at a wavelength 100 nm deeper in the infrared. For in vivo optical applications, it is essential that nanoparticles operate in near infrared wavelengths, so any excitation and emission light avoids scatter and absorption from body tissue. Since the different types of porphysomes absorbed at different wavelengths, they can accommodate applications that are restricted to particular wavelengths. The shifted absorption spectra of the zinc porphysomes indicates that the zinc was fully chelated into the porphysome, since zinc induces a shift in porphyrin absorption. Dynamic light scattering (DLS) was used to assess the size of the various porphysomes. As shown in FIG. 6B, all three types of porphysomes had an excellent size distribution of around 100 nm and formed highly monodisperse nanoparticles. 100 nm porphysomes are highly desirable size since this size is recognized as the optimal size for liposome accumulation in tumours through the enhanced permeability and retention effect[36]. While 100 nm porphysomes may be suitable for some purposes, in other instances it may be desirable to use porphysomes that are smaller and may easily diffuse in and out of all vasculature. Sonication is usually used to produce liposomes that are smaller than 50 nm. To produce smaller porphysomes, a Pyro-lipid film hydrated with water was subjected to sonication for 10 minutes. As shown in FIG. 7, this procedure resulted in stable 30 nm porphysomes, much smaller than the 100 nm porphysomes generated by extrusion. Although DLS indicated the extruded porphysomes were on average 100 nm and monodisperse, more structural details were desired since porphysomes represent a fundamentally new, uncharacterized material and the exact porphysome structure was still not confirmed. Transmission electron microscopy (TEM) was used to examine porphysomes using uranyl acetate as a negative stain. As shown in FIG. 8, the shape of the porphysomes was perfectly spherical, with the features of a porphyrin bilayer clearly visible at higher TEM magnification. The circular shape persisted throughout the harsh staining and imaging processes of TEM, suggesting the porphysomes were highly stable and possessed a well defined spherical structure. Since these vesicles were composed almost completely of conjugated porphyrin lipids, the structures observed are porphyrin bilayers that form spherical nanovesicles 100 nm in diameter.

Figure 9:
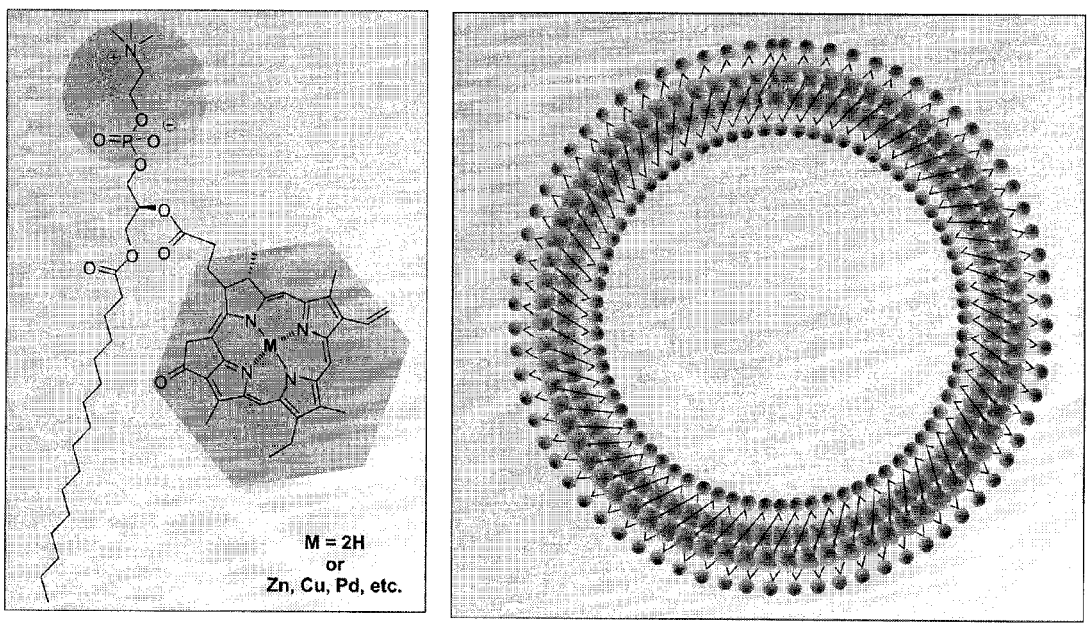
FIG. 9 shows a schematic representation of porphysome subunit and structure. Left panel shows the chemical structure of Pyro-lipid, with the phosphocholine headgroup highlighted in the circle and the porphyrin highlighted in the hexagon. Right panel shows the schematic representation of the porphysome.

Based on the chemical and structural data obtained, a schematic representation of porphysomes is offered in FIG. 9. The Pyro-lipid subunit, chemical structure is shown on the left, with the phosphocholine headgroup highlighted in a red circle and the conjugated porphyrin moiety highlighted in a blue hexagon. The schematic representation of the porphysome structure is shown on the right, using the same subunit colour representation. Previous work has shown there are approximately 100,000 lipids in a 100 nm liposome[37,38]. Because porphysomes have the same headgroup as conventional liposomes, it is expected that porphysomes contain a similar number of subunits per particle. Since the extinction coefficient of pyropheophorbide is quite large (97,000 $M^{-1}$ $cm^{-1}$), assembled porphysomes are estimated to possess an extinction coefficient in the ballpark of $10^9$ or $10^{10} M^{-1} cm^{-1}$. This extinction coefficient is approximately 1000 to 10,000 times greater than that of quantum dots, while porphysomes are only approximately 2-10 times larger in size.

As nanostructures, porphysomes offer many advantages over conventional liposomes with regards to porphyrin loading. Liposomes cannot form with concentrations of free porphyrin higher than about 15 molar %. At such concentrations, the liposomes are unstable and therefore a smaller molar percentage must be used. Porphysomes can achieve a 10-100 fold improvement in porphyrin loading since up to 100 molar % porphyrin may be incorporated. When liposome formulated photosensitizers are administered, the photosensitizer rapidly redistributes to serum proteins, negating the utility of liposome targeting. Porphysomes are stably formed from photosensitizer conjugates and therefore high payload photosensitizer targeting becomes a reality for the first time. Porphysomes offer a 10,000 fold loading improvement over conventional antibody conjugated photosensitizers which are limited to approximately 10 photosensitizers per particle.

Porphysomes are Photosensitizers with Unprecedented Activation Potential

Figure 10:
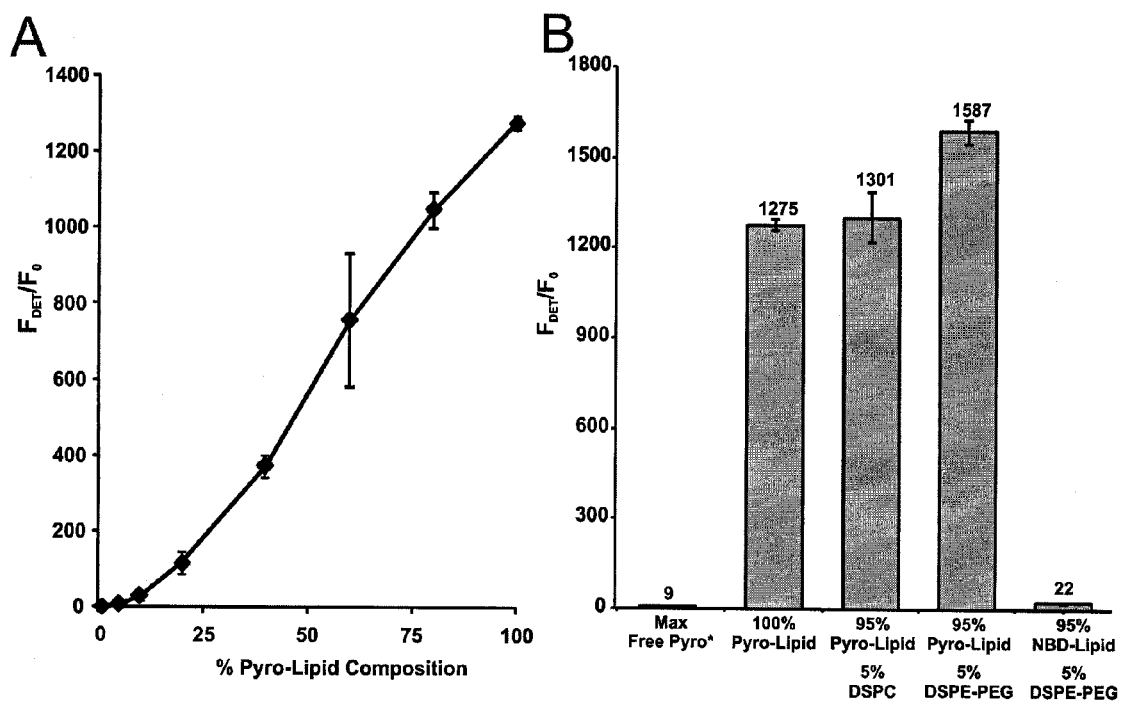
FIG. 10 shows porphysomes displaying remarkable activation potential. A) A titration of Pyro-lipid in PC:Chol (3:2) liposomes. FDET represents the fluorescence after porphysomes were lysed with 0.5% detergent (Triton X-100) and Fo represents the initial fluorescence of the porphysomes. B) Activation of porphysomes is much higher than liposomes with free Pyro or NBD-Lipid. Incorporation of a small amount of PEG lipid generated the highest activation potential.

Since porphysomes have two spherical layers of porphyrin located closely together, they are prone to self quenching prior to cellular incorporation and activation. As shown in FIG. 10A, a titration of Pyro-lipid into standard liposomes consisting of PC:Chol (3:2 ratio) led to an astounding increase in activation potential. Porphysomes composed with 100% Pyro-lipid demonstrated 1300 fold activation upon detergent addition. The increase in activation potential was approximately linear as a function of Pyro-lipid concentration. FIG. 10B shows that liposomes that were formed with the maximum amount of free Pyro (15%) demonstrated only 10 fold activation. Higher percentages of free Pyro incorporation into the lipid films could not be fully solubilised during the film rehydration. This suggests that incorporated free Pyro is oriented randomly in the bilayer whereas the porphyrin bilayer of porphysomes actually stabilizes the nanostructure. Replacing 5% of the Pyro-lipid with DSPC, a lipid with a high transition temperature did not change the activation potential of porphysomes significantly. However, when DSPE-PEG was incorporated, the activation potential increased to greater than 1500 fold. DSPE-PEG also improved the long term stability of porphysomes, which remained stable for over 2 months when stored at 4° C. In addition, PEG is improves drug pharmacokinetics and biodistribution. When Pyro-lipid was replaced with NBD-lipid, a fluorescent tracer lipid that differs in the functional sidechain (Pyro vs NBD), only a 22 fold activation was observed. DLS indicated that stable liposomes could not form using 95 molar % NBD-lipid, emphasizing the stabilizing effect of the porphyrin interactions in generating stable porphysomes.

Biocompatibility of Porphysomes

Figure 19:
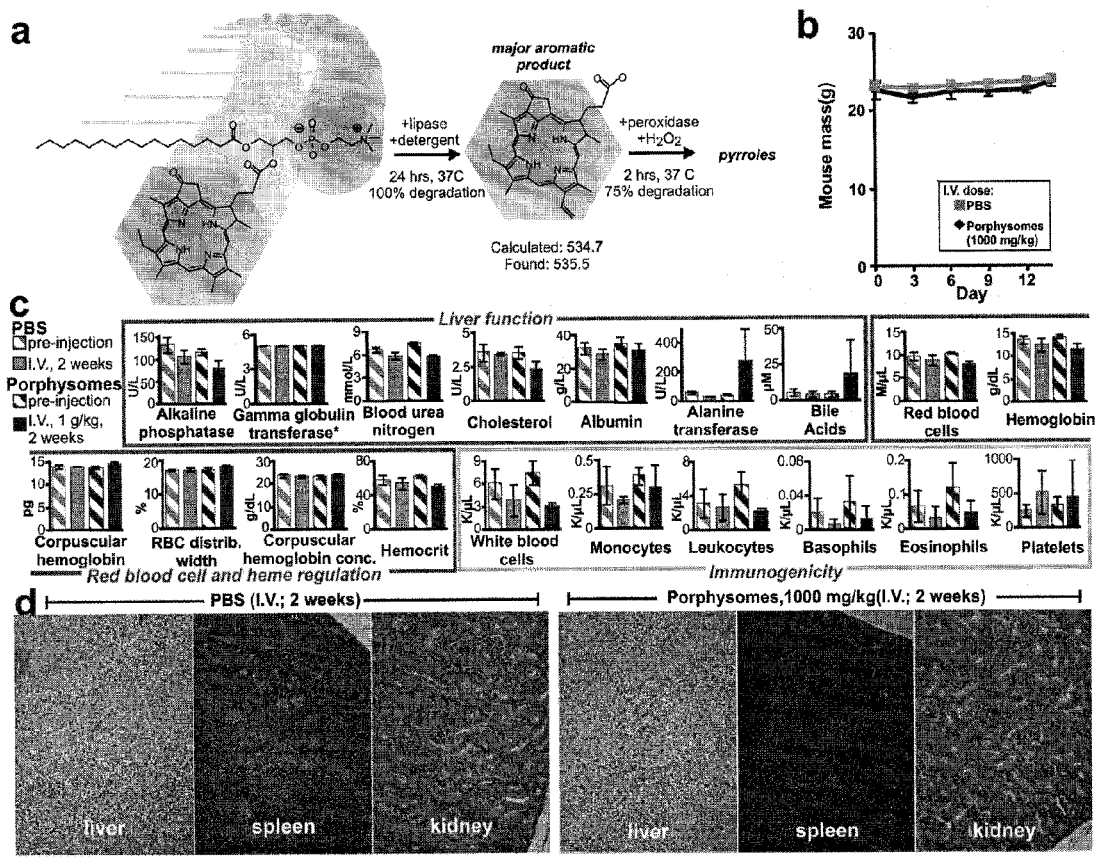
FIG. 19 shows porphysomes are enzymatically biodegradable and well tolerated in vivo. a, Enzymatic degradation of porphysomes. Porphysomes were lysed with 1% Triton X-100 and incubated with lipase in PBS. Degradation was probed using HPLC-MS analysis. Purified pyropheophorbide was incubated with peroxidase and degradation was verified by monitoring the loss of absorbance at 680 nm. b, Mouse mass change after intravenous administration of 1000 mg/kg porphysomes or PBS (mean+/−SD, n=3). c, Blood test parameters for mice with intravenous administration of porphysomes or PBS. (mean+/−SD, n=3). Since some test values for gamma globulin transferase results were given as less than 5 U/L, all values less than 5 U/L are reported as 5 U/L. d, Representative hematoxylin and eosin stained sections of indicated organs from mice 2 weeks after I.V. injection of 1000 mg/kg porphysomes or PBS.

We next assessed factors relevant to potential clinical applications of porphysomes. Porphysomes were prone to enzymatic degradation (FIG. 19a). Upon incubation with detergent and lipase, the phospholipid structure was cleaved, with the major aromatic product being pyropheophorbide, which was the starting material in the synthetic reaction generating the porphyrin-lipid. Like chlorophyll, pyropheophorbide is known to be enzymatically cleaved into colorless pyrroles when incubated with peroxidase and hydrogen peroxide. We verified this degradation by monitoring the loss of porphyrin absorption and confirmed that pyropheophorbide could be efficiently degraded by peroxidase. To our knowledge, this is the first example of an enzymatically biodegradable optically active nanoparticle. We next performed a preliminary study to assess the potential toxicity of porphysomes. When mice were treated with a high dose of porphysomes (1000 mg/kg), they remained generally healthy over a two week period, as demonstrated by a lack of major behavior changes or weight loss (FIG. 19b). At the two week time point, mice were sacrificed and blood tests were performed (FIG. 19c). Liver function tests indicated mice hepatic function was generally normal, with the exception of somewhat elevated bile acids and alanine transferase (less than 2 times the upper range of normal). Red blood cell counts and attributes were unaffected by the large dose of porphyrin-lipid, which did not interfere with the physiological regulation of endogenous porphyrin (heme). Unaffected white blood cell counts imply that porphysomes were not immunogenic at the two week time point, even at the high doses given to mice. Post-mortem histopathological examination of the liver, spleen and kidneys indicated these organs were in good condition and were not impacted by the high intravenous porphysome dose (FIG. 19d).

Loading the Large Aqueous Core of Porphysomes

Figure 20:
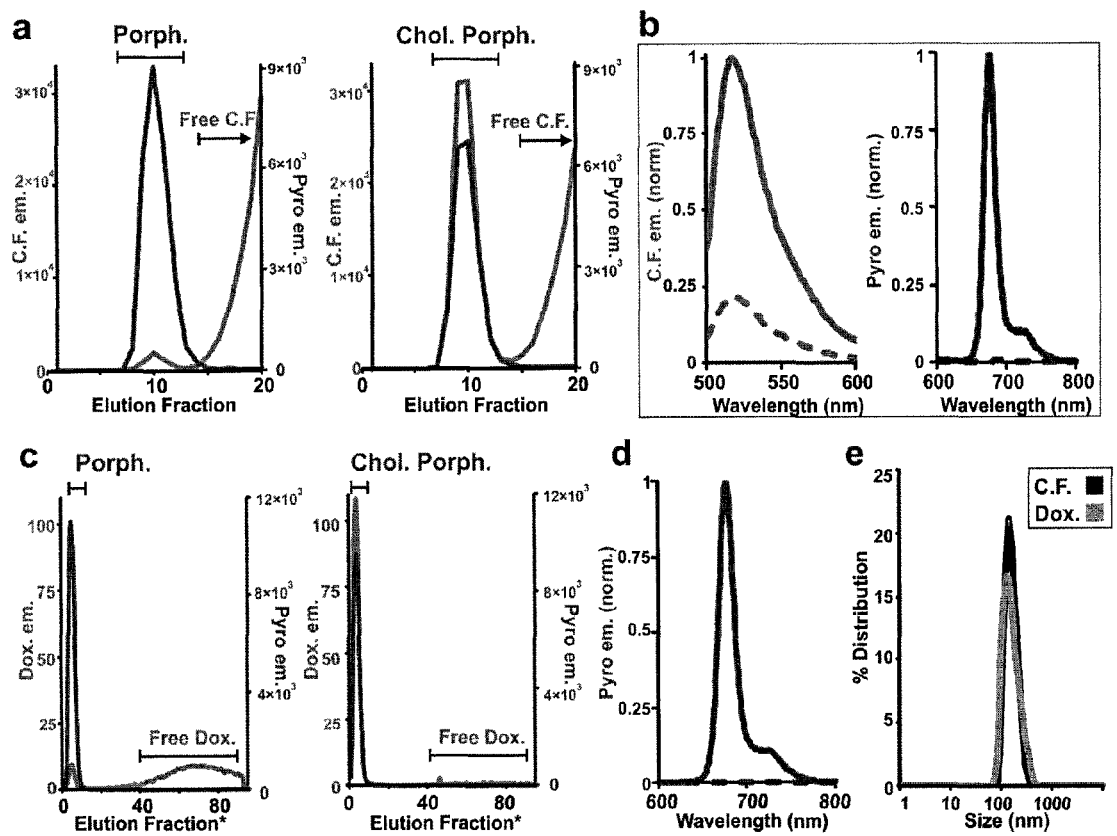
FIG. 20 shows active and passive loading of porphysomes. a, Passive loading loading of carboxyfluorescein (C.F.). Porphysomes composed without (Porph.) or with 30 mol. % cholesterol (Chol. Porph.) were extruded in 250 mM C.F. and gel filtration was performed to determine C.F. incorporation. Fluorescence of Pyro (blue) and C.F. (green) was measured in 0.5% Triton X-100 to avoid quenching. b, Fluorescence quenching of Chol. Porph. (blue) loaded with C.F (green). Spectra were taken prior (dashed line) and after (solid line) addition of 0.5% Triton X-100 and normalized to maximum fluorescence. c, Active loading of doxorubicin (Dox.). with an ammonium sulfate gradient. Fluorescence analysis of gel filtration fractions (*collected when the porphysomes began to elute) of porphysomes without (Porph) or with (Chol. Porph.) 50 mol. % cholesterol. Fluorescence of pyro (blue) and Dox. (green) was measured in 0.5% Triton X-100 to avoid quenching d, Fluorescence quenching of pyro in Chol. Porph. loaded with Dox. Normalized spectrum was measured prior (solid line) and after (dashed line) addition of 0.5% Triton X-100. e, Size distributions of porphysomes passively loaded with C.F. (black line) or actively loaded with doxorubicin (gray line).

One of the most striking observations of the porphyrin bilayer structure is the large aqueous core, which has potential for cargo loading (FIG. 8). Unlike inorganic nanoparticles, such as gold nanoparticles, which generally load cargo through surface adsorption or conjugation, porphysomes are free to fill their entire volume. When porphysomes (containing 5% PEG-lipid) were hydrated using a 250 mM carboxyfluorescein solution and extruded, only a limited amount of carboxyfluorescein was stably entrapped in the porphysomes as determined by gel filtration (FIG. 20a). As cholesterol is known to enhance loading of compounds within phosphatidylcholine-based liposomes, we included 30 molar % cholesterol into the formulation and repeated the passive carboxyfluorescein loading. The cholesterol containing porphysomes were able to load carboxyfluorescein with a high efficiency 20 times greater than the porphysomes lacking cholesterol (FIG. 20a). At this high loading concentration, carboxyfluorescein itself was self-quenched in the porphysome (FIG. 20b, left). Further, the porphysome remained nearly entirely self-quenched (FIG. 20b, right), demonstrating that its characteristic phototransductive behavior was retained. As expected, passive loading of carboxyfluorescein only entrapped a small fraction of the total fluorophore in the hydration solution. One of the most powerful drug loading techniques is active loading, which uses pH or ion gradients to concentrate amphipathic weakly basic molecules into liposomes and polymersomes. The importance of this loading technique is reflected by Doxil®, the first clinically implemented nanoparticle, which is a liposomal formulation of actively loaded doxorubicin. We applied the ammonium sulfate gradient method[43] with a doxorubicin to pyro-lipid molar ratio of 1:5 to actively load doxorubicin into porphysomes. Without addition of cholesterol, some loading of doxorubicin was observed by gel filtration, but the fraction of the total doxorubicin incorporated from the solution was approximately 10% (FIG. 20c). However, when 50 molar % cholesterol was added to the porphysome formulation, strong active loading was achieved and porphysomes loaded 90% of all free doxorubicin in solution into the porphysome core.

Although a large molar % cholesterol was used, its effect on the porphyrin density was limited because cholesterol is predicted to occupy only a quarter of the space of phosphatidylcholine subunits[44] and thus only marginally reduced porphyrin bilayer density. This is supported by the maintained extreme porphyrin self-quenching demonstrated in FIG. 20d. In addition to having similar phototransductive properties as unloaded porphysomes, both actively and passively loaded porphysomes maintained monodispersity and displayed sizes between 150 nm and 200 nm (FIG. 20e).

Porphysomes as Phototransducers

Figure 11:
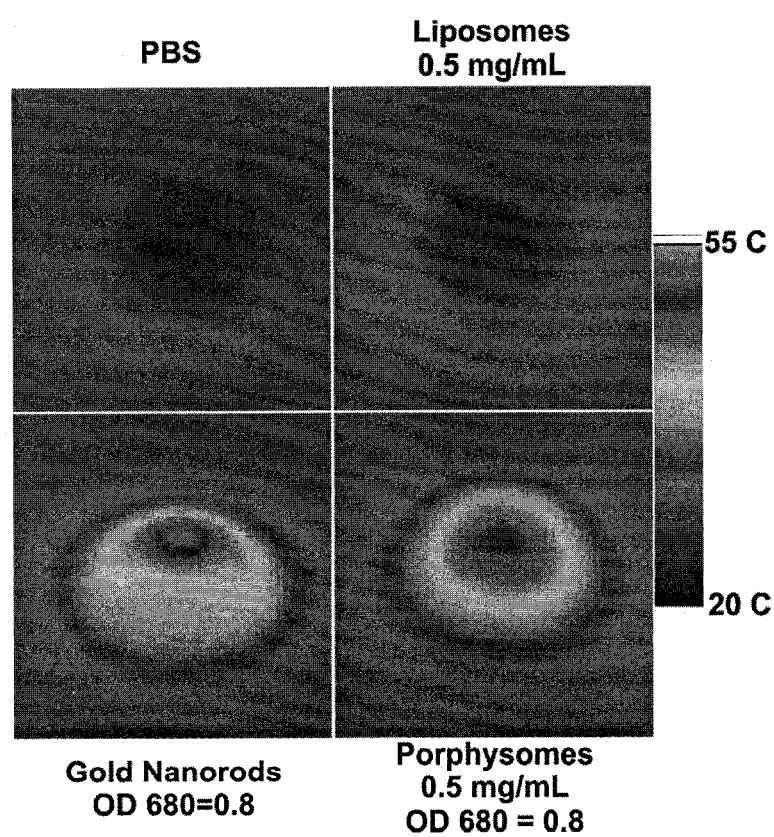
FIG. 11 shows efficient photothermal transduction by porphysomes. 5 uL drops were irradiated with a 150 mW 670 nm laser and imaged with an infrared camera. Liposomes were formed with a standard PC:Chol (3:2) composition. Spectrum legend on the right side shows violet at 20 C and proceeding through indigo, blue, green, yellow, orange to red and pink at 55 C. Top two panels, PBS and Liposomes, shows blue centers. Bottom two panels, gold nanorods and prophysomes, show red centers proceeding through orange and yellow to green outer edges.

Photothermal therapy is an area of growing interest, as demonstrated by discoveries such as the high photothermal transduction efficiency of gold nanorods[39]. Because of their large absorption coefficient and highly quenched state prior to cellular uptake, the photothermal properties of porphysomes were investigated (FIG. 11). Using an temperature calibrated infrared camera, it was shown that under laser irradiation of 150 mW using a 670 nm laser, neither PBS nor standard PC:Chol (3:2) liposomes generated a significant photothermal response. When gold nanorods with an absorption of 0.8 at 670 nm were irradiated with the laser, heat was efficiently produced and detected by the infrared camera. When porphysomes with the same absorption were measured, they generated a similar amount of photothermal conversion. Thus, although they generated a similar photothermal effect, porphysomes represent a non metallic and soft nanoparticle that may be useful for hyperthermia and photoacoustic applications.

Figure 12:
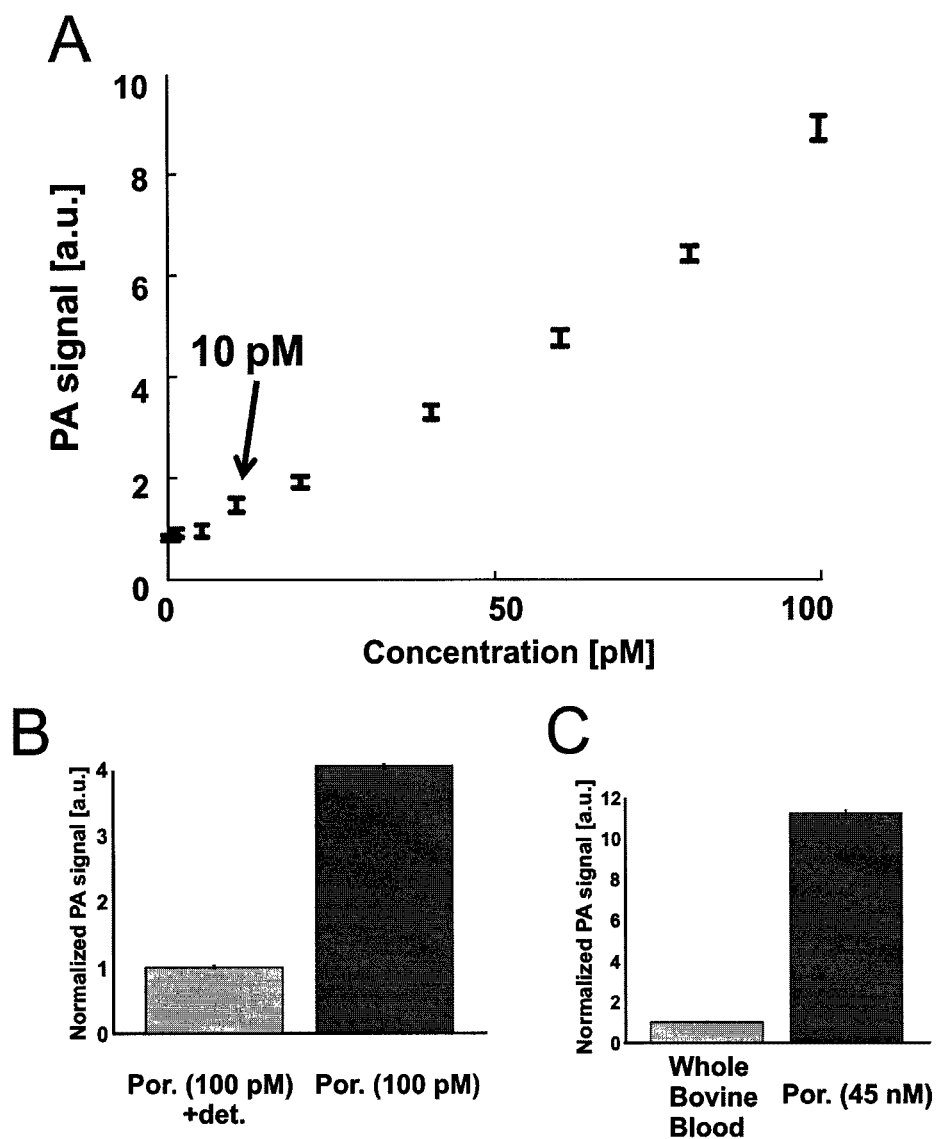
FIG. 12 shows the strong photoacoustic properties of porphysomes. A) Oxybacteriochlorophyll porphysome sensitivity down to low picomolar range at 760 nm. B) Porphysome self assembly generates photoacoustic signal. When the porphysomes were destroyed with detergent, the photoacoustic signal was attenuated, despite having the same amount of absorption in the solution. C) Modest concentrations porphysomes had a signal 11 times greater than whole bovine blood. These porphysome concentrations assume 100,000 porphyrin-lipid molecules per porphysome. Error bars show standard deviation from at least 10 measurements.
Figure 13:
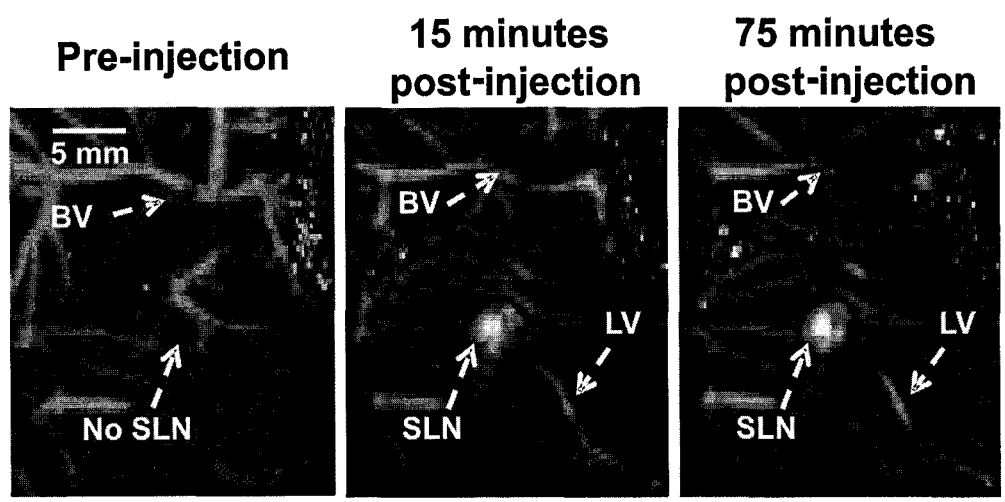
FIG. 13 shows in vivo sentinel lymph node mapping in rats using porphysomes as contrast agents. A) Time course of imaging. BV marks the blood vessels, which are visible prior to porphysome injection intradermally in the paw of the animal. The Sentinel Lymph Node (SLN) and lymph vessles (LV) become readily visible after 15 minutes intradermal injection B) After 2 hours, the rat was sacrificed and the two sentinel lymph nodes on either side of the animal were excised and subjected to photoacoustic tomography. Only the lymph node on the left side where the porphysomes were injected was detectable. Representative data from 3 separate experiments.
Figure 13:
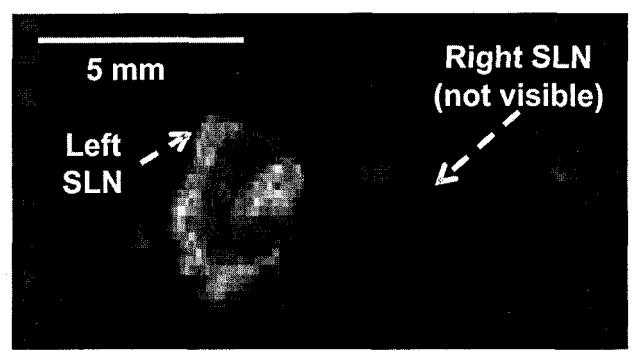

Indeed, porphysomes generated very strong photoacoustic signal when measured in vitro that was detectable down to the low picomolar concentrations and nanomolar concentrations were easily detectable over the signal of blood (FIGS. 12 A and C). Porphysomes have a comparable photoacoustic signal to gold nanoparticles, but have advantages in terms of biocompatibility and drug loading. Furthermore, addition of detergent attenuated the photoacoustic signal, offering direct proof that the self-assembly of subunits is responsible for generating phototransducing properties (FIG. 12B). The utility of porphysomes as photoacoustic probes was verified by using porphysomes to effectively map the sentinel lymph node in rats in vivo (FIG. 13). Detection and examination of sentinel lymph nodes are commonly used steps in evaluating the state of breast cancer metastasis and photoacoustic tomography using porphysomes was an excellent method to detect these sentinel lymph nodes with high signal to noise in vivo. Porphysomes clearly mapped sentinel lymph nodes, independent of targeting ligands (these nodes therefore may or may not contain metastatic cancer). With the appropriate targeting ligand, the porphysomes could additionally be taken up into the cancer cells, which would result in unquenching and the generation of fluorescence.

Figure 14:
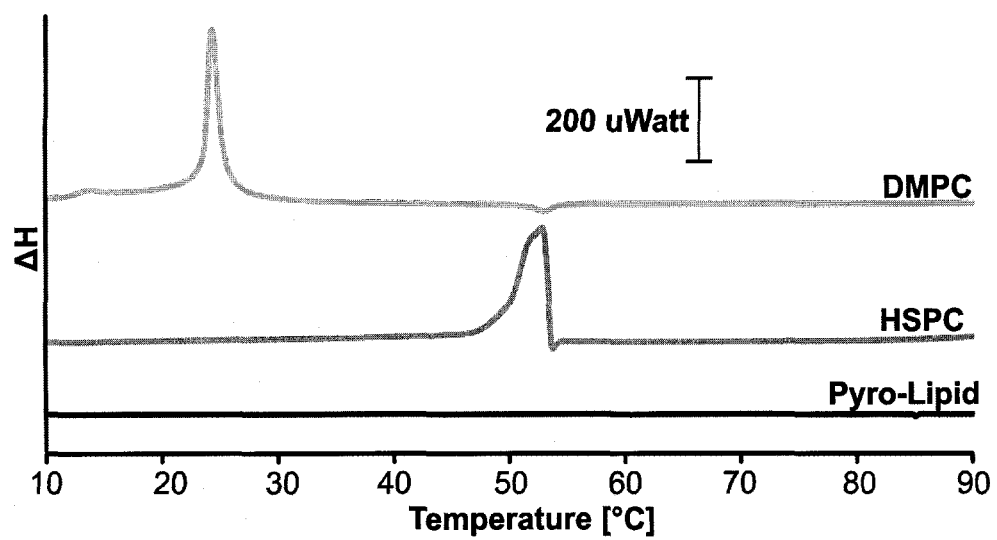
FIG. 14 shows differential scanning calorimetry, revealing that Pyro-lipid does not possess a transition temperature. The DSC was performed in PBS at a lipid concentration of 5 mg/mL.

To further examine the thermal properties of Pyro-lipid, differential scanning calorimetry was used (FIG. 14). Control lipids of DMPC and HSPC behaved as expected, demonstrating transition temperatures of 24° C. and 52° C., respectively. Interestingly, Pyro-lipid displayed no distinct transition temperature, suggesting porphysomes may not be prone to the transition temperatures that occur when lipids change phases. After heating to 95° C. for 15 minutes and cooling back to room temperature, porphysomes retained a good size distribution of approximately 100 nm. Taken together, these data show that porphysomes are both thermally stable and good photothermal and photoacoustic transducers.

Figure 15:
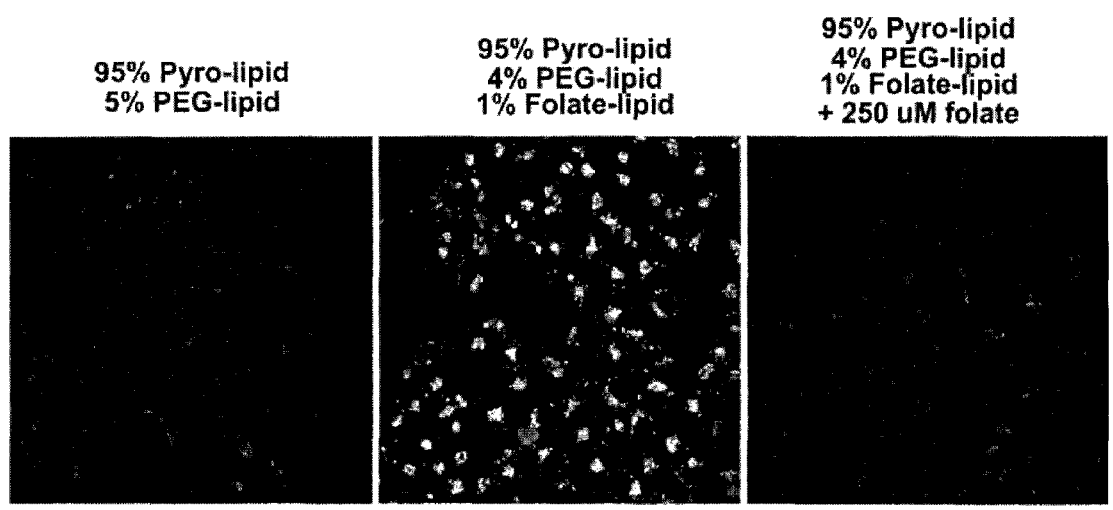
FIG. 15 shows live cell imaging of targeted activation of porphysomes via folate ligand targeting. KB cells were incubated the indicated porphysomes for 2 hours before confocal microscopy.
Figure 16:
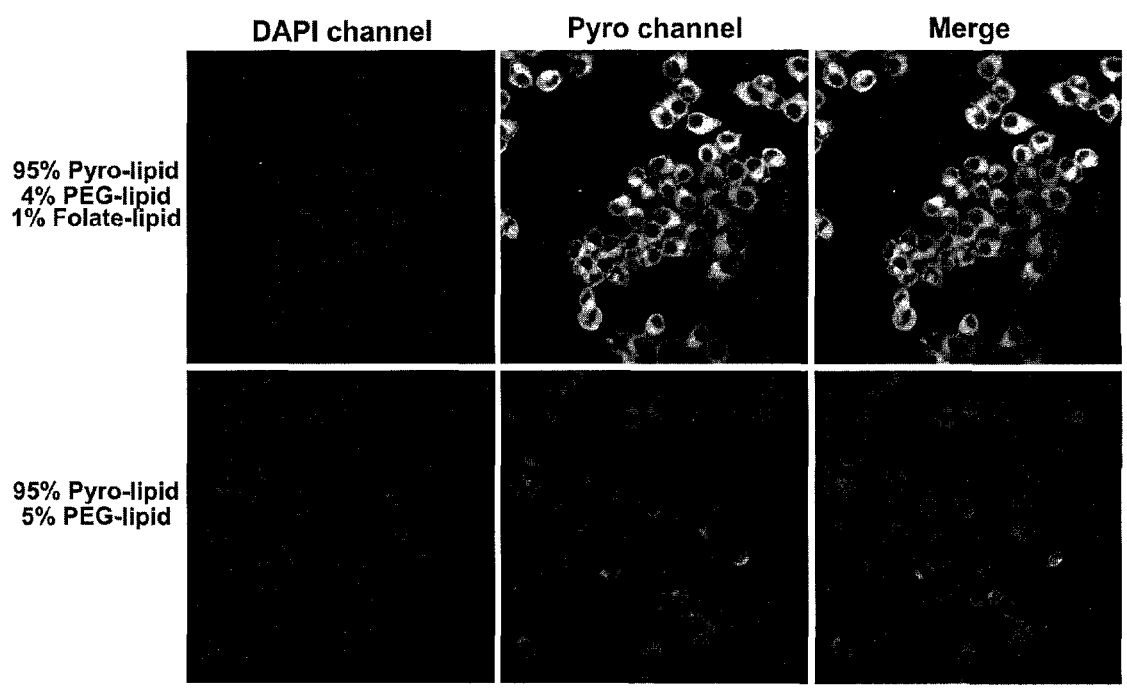
FIG. 16 shows fixed cell imaging of porphysome uptake in folate receptor expressing cells. KB cells were incubated the indicated porphysomes for 2 hours before confocal microscopy. Nuclei were stained with DAPI.
Figure 18:
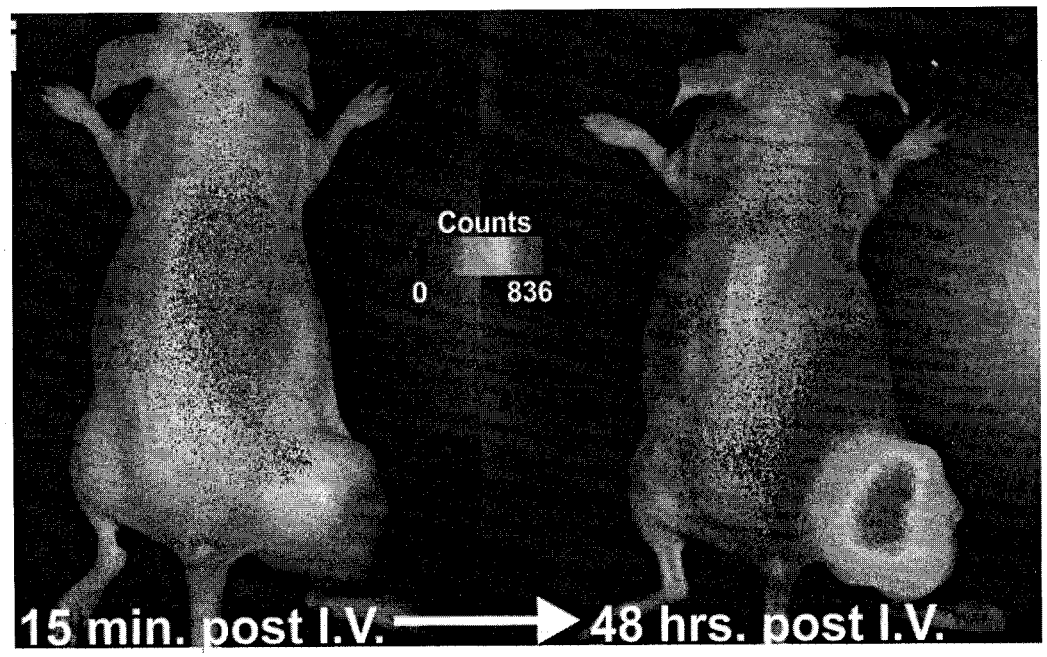
FIG. 18 shows fluorescence activation after I.V. injection of porphysomes (7.5 pmols) in KB xenograft-bearing mouse. Note that after injection, there is little fluorescence signal from the mouse, indicating the porphysomes were quenched. After tumor uptake, the porphysomes were unquenched and fluorescence was detectable in the tumor.

While porphysomes possess a remarkably high payload of porphyrin photosensitizers, in their inactive state they exhibit highly quenched fluorescence, suggesting singlet oxygen production is also quenched[40]. To show that porphysomes can be targeted and activated in cells, we targeted the folate receptor, a receptor overexpressed in many cancers[41]. KB cancer cells were used, as they are well known to express the folate receptor[42]. Folate porphysomes were generated by incorporating 1 molar % folate-PEG lipid, 4 molar % PEG-lipid and 95% Pyro-lipid. Porphysome uptake was examined using live cell confocal microscopy. As shown in FIG. 15, when folate-tagged porphysomes were incubated with KB cells for two hours, not only were the porphysomes taken up by the cells, the high fluorescence signal indicates that the porphysomes were activated upon uptake, since they are essentially non fluorescent prior to activation. The mechanism of activation may be that the porphysomes disassemble during endocytosis. Since fluorescence dequenching is correlated to singlet oxygen dequenching, the porphysomes presumably increased their single oxygen response upon specific targeting. Porphysomes lacking the folate targeting moiety displayed minimal uptake. When cells were incubated with an excess of folic acid, folate tagged porphysomes were not taken up efficiently, showing the specificity of the uptake mechanism. We also examined porphysome uptake using nuclear staining and fixed cell imaging (FIG. 16). The uptake of porphysomes again was dependent on folate conjugation. As with the live cell imaging, the porphysomes were excluded from the nucleus, however, in fixed cell imaging, the porphysome distribution in the cell was much more homogenous. This may indicate that in live cells porphysomes are compartmentalized into endosomes at the two hour time point and further time may be required for porphysome redistribution in the cell. When porphysomes were injected intravenously in tumor bearing mice, initially there was negligible fluorescence in the mouse (FIG. 18, left). This demonstrates the porphysomes were quenched in vivo initially. Over time, porphysomes accumulated in the tumor and were unquenched (FIG. 18, right). This demonstrates that porphysomes can be used as low background probes for fluorescence imaging (and also photodynamic therapy).

Figure 17:
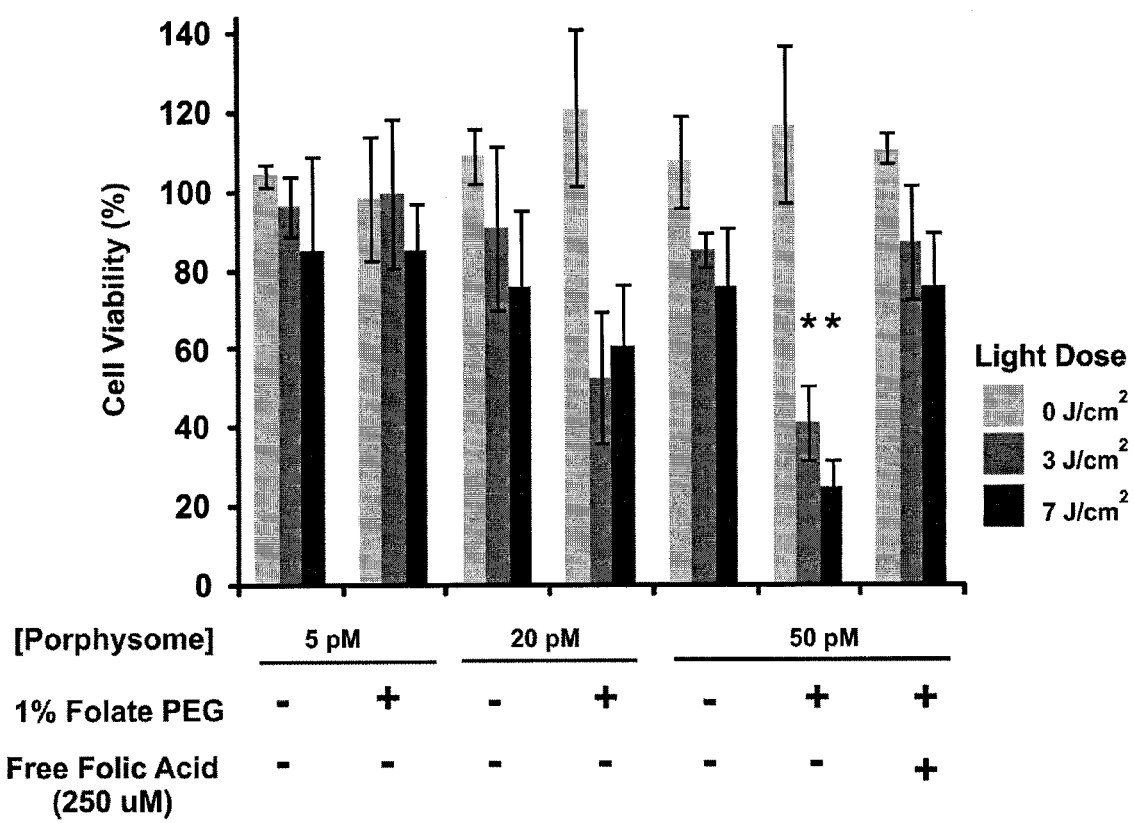
FIG. 17 shows PDT treatment with targeted porphysomes. KB cells were incubated with folate conjugated porphysomes or regular porphysomes for 4 hours then treated with a 670 nm laser at the indicated light doses. The next day, cell viability was assessed using the MTT assay. Porphysome concentration was based on the assumption of 100,000 porphyrin-lipid molecules per porphysome. Asterisk shows that high light fluence and porphysome concentration generated the most cell killing. Error bars show standard deviation with n=4.

To show that porphysomes can kill cells via specific and molecularly targeted mechanism, KB cells were incubated with porphysomes containing or not containing 1 molar % folic acid targeting lipid. The cells were then exposed to varying intensities of laser irradiation. As shown in FIG. 17, porphysome mediated cell killing was dose responsive to both porphysome concentration as well as light dose strength. Folic acid lipid incorporation into porphysomes was required for effective PDT. Consistent with the confocal microscopy results, folate-targeted porphysome mediated PDT cell killing was inhibited when an excess of free folate was added during the incubation, confirming the specificity of the porphysome targeting and killing.

Figure 21:
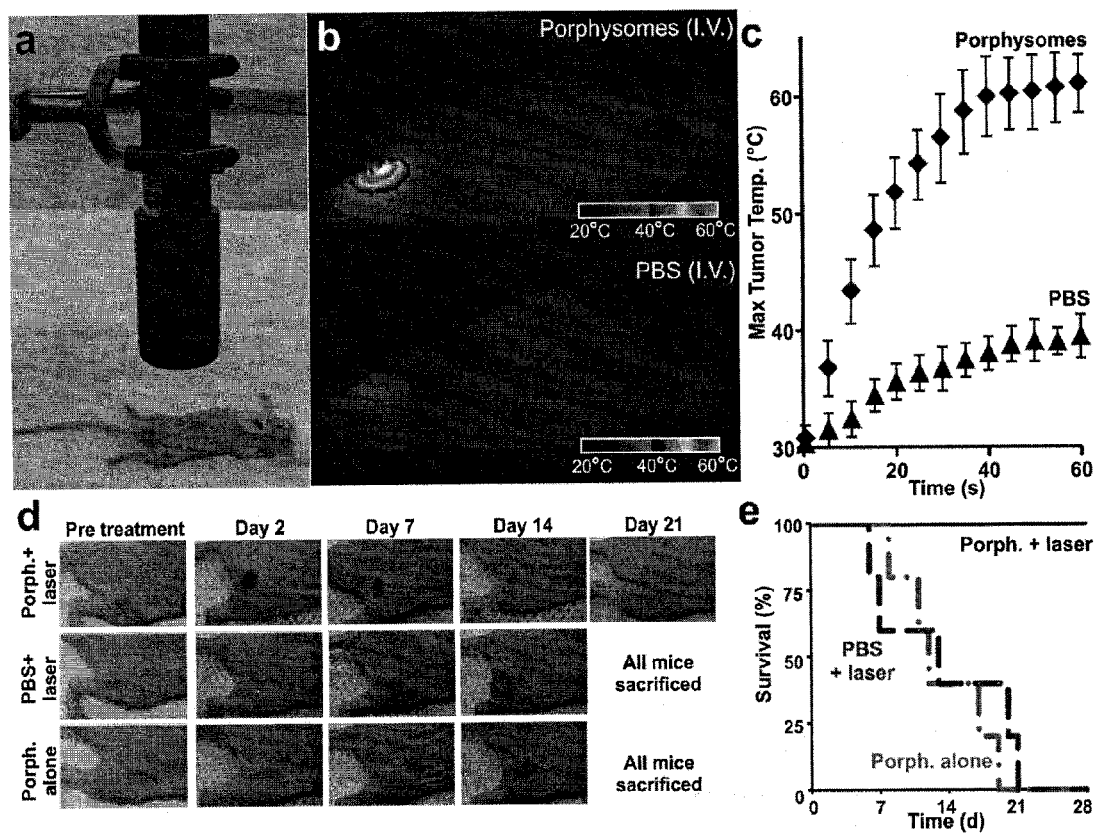
FIG. 21 shows porphysomes as photothermal transducers in vivo. a, Photothermal therapy setup using a portable 660 nm laser. b, Representative thermal response in KB tumor-bearing mice injected I.V. 24 hours prior with PBS or 42 mg/kg porphysomes. Thermal image was obtained after 60 seconds of laser irradiation (1.9 W/cm$^2$) c, Maximum tumor temperature during 60 second laser irradiation (mean+/−SD for 5 mice per group). d, Photographs demonstrating therapeutic response to photothermal therapy using porphysomes. e) Survival plot of tumor bearing mice treated with the indicated conditions. Mice were sacrificed when tumors reached 10 mm size (n=5 for each group).

To demonstrate the biophotonic therapeutic potential of an organic nanoparticle, we next performed preliminary experiments using porphysomes as agents for photothermal therapy. A 658 nm laser outputting 750 mW (with a power density of 1.9 W/cm$^2$) was used to irradiate the KB tumors in xenograft bearing mice following porphysome administration (FIG. 21a). 24 hours prior to treatment, mice were injected intravenously with 42 mg/kg porphysomes. 24 hours following administration of porphysomes or PBS, the tumor was irradiated with the laser for 1 minute and temperature was monitored using a thermal camera (FIG. 21b). The tumor temperature in the porphysome group rapidly reached 60° C., whereas the tumors in mice injected with PBS were limited to 40° C. (FIG. 21c). Following treatment, mice in the porphysome and laser treated group developed eschars on the tumors, whereas the laser alone group and the porphysomes alone group did not. After 2 weeks the eschars healed and the tumors in the treated group were permanently destroyed (FIG. 21d). Unlike the tumors in mice treated with porphysomes and light, tumors in mice that received laser treatment alone or porphysome injection alone continued to grow rapidly and all the mice in those groups had to be euthanized within 21 days (FIG. 21e). This photothermal experiment corresponded to a treatment with a therapeutic index of at least 25, given the safety of porphysomes at 1 g/kg intravenous doses.

CONCLUSION

New nanoparticles and the novel properties they carry are the driving force behind the growing nanotechnology revolution. Porphysomes represent a fundamentally different type of nanoparticle that possesses novel nanoscale properties that are well suited for therapeutic applications. Porphysomes are versatile and can be generated with varying optical and size properties. Porphysomes can be formed with a metal chelated bilayer, representing a new avenue for targeted metal delivery. Since each porphysome is an assembly of approximately 100,000 photosensitizers, porphysomes can carry an unparalleled photosensitizer payload for PDT. Furthermore, they are targetable, an attribute that has not been present for conventional liposomal formulations of photo sensitizers. Porphysomes are activated upon cellular uptake, with up to 1000 fold increase in fluorescence upon activation. Porphysomes display photothermal transduction efficiency in the same range as gold nanorods, the current standard for photothermal conversion, but unlike nanorods, porphysomes are of organic nature that is biodegradable and well tolerated in vivo. Unlike other optically active nanoparticles, the large aqueous core of porphysomes can be loaded with fluorophores and drugs. Along with multimodal photonic imaging capabilities, porphysomes have great therapeutic potential based on their intrinsic suitability for drug loading and photodynamic and photothermal therapy.

Although preferred embodiments of the invention have been described herein, it will be understood by those skilled in the art that variations may be made thereto without departing from the spirit of the invention or the scope of the appended claims. All references following and mentioned herein are incorporated in their entirety by reference.

REFERENCES

1. Chan, W. C. W. & Nie, S. *Science* 281, 2016-2018, 1998.
2. Storhoff, J. J., Lucas, A. D., Garimella, V., Bao, Y. P. & Müller, U. R. *Nat. Biotechnol.* 22, 883-887, 2004.
3. Dolmans, D. E., Fukumura, D. & Jain, R. K. *Nat. Rev. Cancer* 3, 380-387, 2003.
4. O'Neal, D. P., Hirsch, L. R., Halas, N. J., Payne, J. D. & West, J. L. *Cancer Lett.* 209, 171-176 2004.
5. Huang, X., El-Sayed, I. H., Qian, W. & El-Sayed, M. A. *J. Am. Chem. Soc.* 128, 2115-2120, 2006.
6. Oraevsky, A. A. *Proc. SPIE* 2676, 22-31, 1996.
7. Oraevsky, A. A. & Karabutov, A. A. *Biomedical Photonics Handbook*, 2003 ed.; Vo-Dinh, T., Ed.; CRC Press: Boca Raton, 34.1-34.34, 2003.
8. Xu, M. & Wang, L. V. *Rev. Sci. Instrum.* 77, 041101 2006.
9. Wang, L. V. *Nat. Photonics* 3, 503-509, 2009.
10. Vakoc, B. J. et al. *Nat. Med.* 15, 1219-1223, 2009.
11. Weissleder, R. & Pittet, M. J. *Nature* 452, 580-589, 2008.
12. Klostranec, J. M. & Chan, W. *Adv. Mater.* 18, 1953-1964, 2006.
13. Yguerabide, J. & Yguerabide, E. E. *Anal. Biochem.* 262, 137-156, 1998.
14. Lal, S., Clare, S. E. & Halas, N. J. *Accounts of Chemical Research* 41, 1842-1851, 2008.
15. Ghosh, P. *Advanced Drug Delivery Reviews* 60, 1307-1315, 2008.
16. Lewinski, N., Colvin, V. & Drezek, R. *Small* 4, 26-49, 2008.
17. Nel, A., Xia, T., Madler, L. & Li, N. *Science* 311, 622-627, 2006.
18. Peer, D. et al. *Nat. Nanotechnol.* 2, 751-760, 2007.
19. Drain, C. M., Varotto, A. & Radivojevic, I. *Chem. Rev.* 109, 1630-1658, 2009.
20. Komatsu, T., Moritake, M., Nakagawa, A. & Tsuchida, E. *Chem. Eur. J.* 8, 5469-5480, 2002.
21. Ghoroghchian, P. P. et al. *Proc. Natl. Acad. Sci. U.S.A.* 102, 2922-2927, 2005.
22. Woodburn, K. W.; Engelman, C. J.; Blumenkranz & M. S. *Retina* (Philadelphia, Pa.), 22, 391-405, 2002.
23. Babilas, P.; Karrer, S.; Sidoroff, A.; Landthaler, M. & Szeimies, R. *Photodermatology, Photoimmunology Photomedicine*, 21, 142-149, 2005.
24. Brown, S. B. *Lancet Oncology*, 5, 508, 2004.
25. Dougherty, T., et al., *J. Natl. Cancer Inst.*, 90, 889-905, 1998.
26. Sternberg, E. D.; Dolphin, D. & Brückner, C. *Tetrahedron* 54, 4151-4202, 1998.
27. Chen, B.; Pogue, B. W. & Hasan, T. *Expert Opin. Drug Deliv.* 2, 477-487, 2005.
28. Miller, G. G.; Lown & J. W. *Drug Dev. Res.* 42, 182-197, 1997.
29. Matos, M. S. et al., *Macromolecules* 33, 2967-2973, 2000.
30. Tsuda, A. & Osuka, A., *Science* 293, 79-82, 2001.
31. Wang, L.; Liu, H. & Hao, J. *Chem. Comm.* 1353, 2009.
32. Mason, J. T.; Broccoli, A. V. & Huang, C. *Anal. Biochem.* 113, 96-101, 1981.
33. Zheng, G. et al. *Bioconj. Chem.* 13, 392-396, 2002.
34. Biesaga, M.; Pyrzynska, K.; Trojanowicz, M. *Talanta* 51, 209-224, 2000.
35. Papahadjopoulos et al., *Proc. Natl. Acad. Sci. U.S.A.* 88, 11460-11464, 1991.
36. Nagayasu, A.; Uchiyama, K. & Kiwada, H. *Advanced Drug Delivery Rev.* 40, 75-87, 1999.
37. Schnyder, A.; Krähenbühl, S.; Török, M.; Drewe, J. & Huwyler, J. *Biochem. J*, 377, 61-67, 2004.
38. Shi, N. & Pardridge, W. M. *Proc. Natl. Acad. Sci. U.S.A.* 97, 7567-7572, 2000.
39. Huang, X.; El-Sayed, I. H.; Qian, W. & El-Sayed, M. A. *J. Am. Chem. Soc.* 128, 2115-2120, 2006.
40. Lovell, J. F et al. *J. Phys. Chem. B* 113, 3203-3211, 2009.
41. Sudimack, J. & Lee, R. J. *Advanced Drug Delivery Rev.* 41, 147-162, 2000.
42. Lee, R. J. & Low, P. S. *J. Biol. Chem.* 269, 3198-3204, 1994.
43. Haran, G., Cohen, R., Bar, L. K. & Barenholz, Y. *Biochimica et Biophysica Acta—Biomembranes* 1151, 201-215, 1993.
44. Hansen, C. B., Kao, G. Y., Moase, E. H., Zalipsky, S. & Allen, T. M. *Biochimica et Biophysica Acta Biomembranes* 1239, 133-144, 1995.

The invention claimed is:

1. A nanovesicle comprising a bilayer of at least 35 molar % porphyrin-phospholipid conjugate, wherein the porphyrin-phospholipid conjugate comprises one porphyrin, porphyrin derivative or porphyrin analog covalently attached to a lipid side chain, preferably at the sn-1 or the sn-2 position, of one phospholipid, wherein the porphyrin, porphyrin derivative or porphyrin analog in the porphyrin-phospholipid conjugate is selected from the group consisting of hematoporphyrin, protoporphyrin, tetraphenylporphyrin, a pyropheophorbide, a bacteriochlorophyll, chlorophyll a, a benzoporphyrin derivative, a tetrahydroxyphenyl chlorin, a purpurin, a benzochlorin, a naphthochlorin, a verdin, a rhodin, a keto chlorin, an azachlorin, a bacteriochlorin, a tolyporphyrin, a benzobacteriochlorin, an expanded porphyrin and a porphyrin isomer.

2. The nanovesicle of claim 1 comprising at least 45, 55, 65, 75, 85 or 95 molar % porphyrin-phospholipid conjugate.

3. The nanovesicle of claim 1, wherein the expanded porphyrin is a texaphyrin, a sapphyrin or a hexaphyrin and the porphyrin isomer is a porphycene, an inverted porphyrin, a phthalocyanine, or a naphthalocyanine.

4. The nanovesicle of claim 1 wherein the phospholipid in the porphyrin-phospholipid conjugate comprises phosphatidylcholine, phosphatidylethanoloamine, phosphatidylserine or phosphatidylinositol.

5. The nanovesicle of claim 4, wherein the phospholipid comprises an acyl side chain of 12 to 22 carbons.

6. The nanovesicle of claim 1 wherein the porphyrin in the porphyrin-phospholipid conjugate is pyropheophorbide-a acid.

7. The nanovesicle of claim 1 wherein the porphyrin in the porphyrin-phospholipid conjugate is a bacteriochlorophyll derivate.

8. The nanovesicle of claim 1 wherein the phospholipid in the porphyrin-phospholipid conjugate is 1-Palmitoyl-2-Hydroxy-sn-Glycero-3-Phosphocholine.

9. The nanovesicle of claim 1 wherein the porphyrin-phospholipid conjugate is oxy-bacteriochlorophyll-lipid.

10. The nanovesicle of claim 1 wherein the porphyrin is conjugated to the glycerol group on the phospholipid by a carbon chain linker of 0 to 20 carbons.

11. The nanovesicle of claim 1 further comprising Polyethylene glycol (PEG).

12. The nanovesicle of claim 11 wherein the PEG is present in an amount of about 5 molar %.

13. The nanovesicle of claim 1 further comprising PEG-lipid.

14. The nanovesicle of claim 1 further comprising PEG-DSPE.

15. The nanovesicle of claim 1, wherein the nanovesicle is substantially spherical and between about 30 nm at about 200 nm in diameter.

16. The nanovesicle of claim 1, wherein the nanovesicle is substantially spherical and about 100 nm in diameter.

17. The nanovesicle of claim 1, wherein the nanovesicle is substantially spherical and about 30 nm in diameter.

18. The nanovesicle of claim 1, wherein the porphyrin-phospholipid conjugate comprises a metal chelated therein, optionally a radioisotope of a metal.

19. The nanovesicle of claim 18 wherein the metal is selected from the group consisting of Zn, Cu and Pd.

20. The nanovesicle of claim 1, further comprising an active agent encapsulated therein, preferably a therapeutic agent or a diagnostic agent, preferably a chemotherapy agent such as doxorubicin.

21. The nanovesicle of claim 1, further comprising a targeting molecule, preferably an antibody, peptide or aptamer.

22. The nanovesicle of claim 21, wherein the targeting molecule is folic acid.

23. The nanovesicle of claim 1, wherein the bilayer further comprises cholesterol, preferably between 30-50 molar % cholesterol.

* * * * *